(12) United States Patent
Splinter et al.

(10) Patent No.: US 11,215,718 B2
(45) Date of Patent: Jan. 4, 2022

(54) SYSTEM AND METHOD FOR SAMPLING FREQUENCY ADJUSTMENT FOR RADIATION IMAGING SYSTEM

(71) Applicant: Analogic Corporation, Peabody, MA (US)

(72) Inventors: Patrick Richard Splinter, Kingston, MA (US); Steven Dana Weed, Marblehead, MA (US); David Gino Vacca, Salem, NH (US); Sevag Minas Zoboyan, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 16/497,630

(22) PCT Filed: Mar. 30, 2017

(86) PCT No.: PCT/US2017/025011
§ 371 (c)(1),
(2) Date: Sep. 25, 2019

(87) PCT Pub. No.: WO2018/182616
PCT Pub. Date: Oct. 4, 2018

(65) Prior Publication Data
US 2021/0109238 A1    Apr. 15, 2021

(51) Int. Cl.
*A61B 6/00* (2006.01)
*G01T 1/164* (2006.01)
(Continued)

(52) U.S. Cl.
CPC ............... *G01T 1/249* (2013.01); *A61B 6/58* (2013.01); *G01T 1/1642* (2013.01); *A61B 6/035* (2013.01)

(58) Field of Classification Search
CPC ......... A61B 6/035; A61B 6/58; G01T 1/1642; G01T 1/249
See application file for complete search history.

(56) References Cited

U.S. PATENT DOCUMENTS 4,620,313 A     10/1986   Erker
2013/0287165 A1*  10/2013  Sharpless ............... A61B 6/547
                                                378/19
(Continued)

FOREIGN PATENT DOCUMENTS

EP     2489310 A     8/2012
WO     2018/182616 A1   10/2018

OTHER PUBLICATIONS

Written Opinion of the International Searching Authority for PCT Application No. PCT/US2017/025011 dated Dec. 18, 2017, 5 pages.

(Continued)

*Primary Examiner* — Mark R Gaworecki
(74) *Attorney, Agent, or Firm* — TraskBritt

(57) ABSTRACT

Among other things, one or more techniques and/or systems are described for setting a sampling frequency for a radiation imaging system. The radiation imaging system comprises a rotating gantry configured to rotate a radiation source and a detector array about an object to generate an image(s) of the object. A data acquisition system is configured to sample the detector array as views. One or more flag structures are arranged according to a partial arc segment (e.g., a structure less than a full 360 degree circle). One or more sensors are disposed on one of the rotating gantry or a stationary support about which the rotating gantry rotates. When a sensor encounters a flag structure, a current rotational speed of the rotating gantry is determined. A clock frequency is updated based upon the current rotational speed to establish a sampling frequency for the data acquisition system for sampling the detector array.

20 Claims, 14 Drawing Sheets

(51) Int. Cl.
*G01T 1/24* (2006.01)
*A61B 6/03* (2006.01)

(56) References Cited

U.S. PATENT DOCUMENTS

2016/0166228 A1  6/2016  Li
2016/0299088 A1  10/2016  Zoboyan et al.

OTHER PUBLICATIONS

International Search Report for PCT Application No. PCT/US2017/025011 dated Dec. 18, 2017, 5 pages.

* cited by examiner

SYSTEM AND METHOD FOR SAMPLING FREQUENCY ADJUSTMENT FOR RADIATION IMAGING SYSTEM

CROSS-REFERENCE TO RELATED APPLICATIONS

This application is a national phase entry under 35 U.S.C. § 371 of International Patent Application PCT/US2017/025011, filed Mar. 30, 2017, designating the United States of America and published as International Patent Publication WO 2018/182616 A1 on Oct. 4, 2018.

TECHNICAL FIELD

The present disclosure relates to the field of radiation imaging systems. It finds particular application with the triggering of a data acquisition system of a radiation imaging system according to a sampling frequency that is adjusted dynamically during a revolution of a rotating gantry relative to an object under examination.

BACKGROUND

Today, radiation imaging systems such as computed tomography (CT) systems, single-photon emission computed tomography (SPECT) systems, projection systems, and/or line-scan systems, for example, are useful to provide information, or images, of interior aspects of an object under examination. Generally, the object is exposed to radiation comprising photons (e.g., x-rays, gamma rays, etc.), and an image(s) is formed based upon the radiation absorbed and/or attenuated by interior aspects of the object, or rather an amount of radiation photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation imaging systems typically comprise a detector array having one or more detector cells. Respective detector cells are configured to indirectly or directly convert radiation photons impingent thereon into an electrical charge that is used to generate an electrical signal. The detector cells are typically "charge integrating" or "photon counting" type detector cells (e.g., the radiation imaging system operates in charge integrating mode or photon counting mode).

Charge integrating detector cells, also referred to as energy integrating detector cells, are configured to integrate the electrical charge generated over a period of time (e.g., at times referred to as a integration period or view) to generate a signal that is proportional to an incoming radiation photon flux rate at a detector cell. A tick fence is often used to define the integration period. The tick fence comprises physical markers that are disposed on a stationary support and are detected or measured by a sensor on the rotating gantry. As the gantry rotates, the data acquisition system encounters the physical markers, which triggers the data acquisition system to perform an integration (e.g., readout the charge that has accumulated on respective detector cells and reset the detector cells). In addition to the integration timing, the tick fence provides rotational positioning. The tick fence can also be used for photon counting type detector cells to trigger the sampling of such detector cells.

The tick fence is a single 360 degree structure upon which the physical markers are embodied. The 360 degree structure is machined in a 360 degree hoop and is installed onto the stationary support, which is mechanically difficult to implement, install, and maintain. For example, there may be no easy access to the full 360 degree structure to clean out dirt and perform maintenance. Alignment issues of the 360 degree structure can cause trigger timing issues or even damage to physical markers and/or sensors. Moreover, fabrication of the 360 degree structure is costly due to the 360 degree design, and some radiation imaging systems do not have a full 360 frame upon which to mount the 360 degree structure. Thus there is no adequate physical structure upon which the 360 degree structure can be mounted.

BRIEF SUMMARY

Aspects of the present disclosure address the above matters, and others. According to one aspect, a radiation imaging system is provided. The radiation imaging system comprises a set of sensors disposed on one of a rotating gantry or a stationary support about which the rotating gantry rotates. The radiation imaging system comprises a first flag structure disposed relative to the other of the rotating gantry or the stationary support of the radiation system. The radiation imagining system comprises a data acquisition system. Upon a sensor of the set of sensors encountering the first flag structure, the data acquisition system determines a current rotational speed of the rotating gantry. The data acquisition system sets a clock frequency of a clock based upon the current rotational speed. The clock frequency establishes a sampling frequency for the data acquisition system for samples taken between an encounter with the first flag structure and an encounter with a next flag structure.

According to another aspect, a radiation imaging system is provided. The radiation imaging system comprises an ionizing radiation source. The radiation imaging system also comprises a detector array comprising a plurality of detector cells configured to detect radiation emitted by the ionizing radiation source. The radiation imaging system further comprises a data acquisition system electrically coupled to the detector array and configured to sample the plurality of detector cells according to a sampling frequency. The radiation imaging system comprises a rotating gantry upon which the ionizing radiation source and the detector array are mounted. The radiation imaging system comprises a stationary support. The radiation imaging system comprises a set of sensors disposed on one of the rotating gantry or the stationary support. The radiation imaging system comprises a set of flag structures disposed relative to the other of the rotating gantry or the stationary support and spaced apart to define a partial arc segment. The data acquisition system is configured to determine a current rotational speed of the rotating gantry upon a sensor of the set of sensors encountering a flag structure of the set of flag structures that begins a first partial arc segment portion of the partial arc segment. The data acquisition system is configured to set a clock frequency of a clock based upon the current rotational speed.

According to another aspect, a method for setting a sampling frequency for a radiation imaging system is provided. The method comprises identifying a first pulse detected by a first sensor disposed on one of a rotating gantry or a stationary support about which the rotating gantry rotates. A first current rotational speed of the rotating gantry is determined. A clock frequency of a clock is set based upon the first current rotational speed. The clock frequency establishes a first sampling frequency for a data acquisition system of the radiation imaging system for samples taken between an identification of the first pulse and an identification of a next pulse. A second pulse is detected by a second sensor. The clock frequency of the clock is updated to an updated clock frequency based upon the second current rotational speed. The updated clock frequency establishes a second sampling frequency for the data acquisition system of the radiation imaging system for samples taken between identification of the second pulse and an identification of a second next pulse.

Those of ordinary skill in the art will appreciate still other aspects of the present disclosure upon reading and understanding the appended description.

BRIEF DESCRIPTION OF THE DRAWINGS

The present disclosure is illustrated by way of example and not limitation in the figures of the accompanying drawings, in which like references generally indicate similar elements and in which.

DETAILED DESCRIPTION

Figure 1:
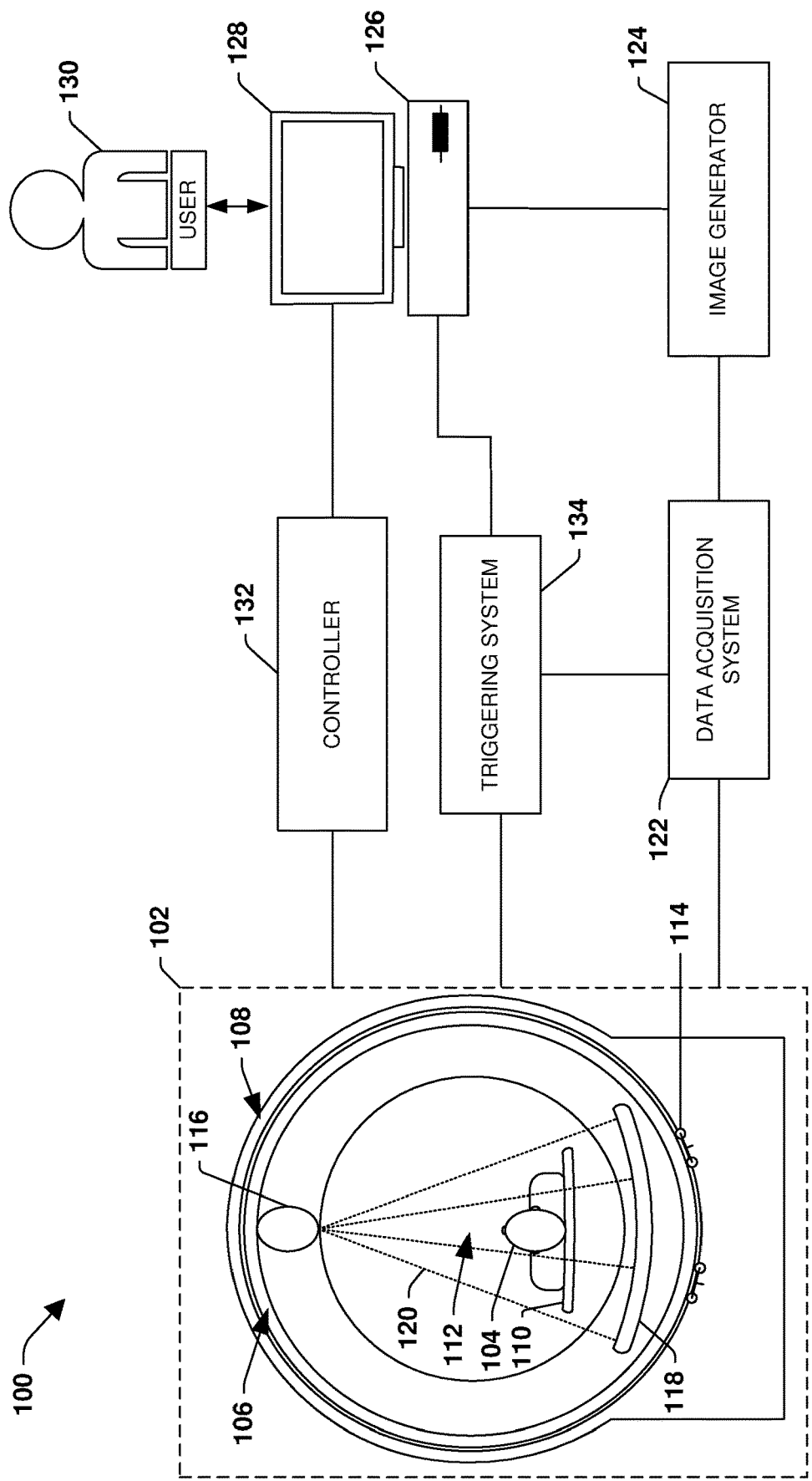
FIG. 1 illustrates an example environment of a radiation imaging system.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Physical markers, such as tick fences, have traditionally been used to trigger sampling of a radiation detector array because the physical markers help ensure that a defined number of samplings occur per period (e.g., a number of integrations performed for charge integration during a full rotation of a rotating gantry). Moreover, the physical markers can be manufactured to enable respective samplings (e.g., views) to represent a substantially same arc length of a revolution. For example, respective integration periods may represent one quarter of one degree of a revolution.

Although triggering sampling based upon physical markers has proven successful, there are challenges to using physical markers. For example, tick fences may be expensive, difficult to mechanically align, susceptible to dust, susceptible to damage from regular service, and/or susceptible to vibration errors affecting position accuracy. Such issues arise from the fact that tick fences are designed with physical markers aligned along a 360 degree structure.

Accordingly, a radiation imaging system, such as a computed tomography (CT) system, comprising a data acquisition system that may be triggered according to a sampling frequency that is adjusted dynamically when a sensor encounters a flag structure, is provided for herein. It may be appreciated that the flag structure may be used for a photon counting system, a charge integration system, etc. One or more flag structures are disposed along a partial arc segment (e.g., a 90 degree arc segment or any other structure that is less than a full 360 degree circular structure) with respect to one of a rotating gantry or a stationary support. One or more sensors, such as optical sensors, are disposed on the other of the rotating gantry or the stationary support. When a sensor encounters (e.g., traverses) a flag structure (e.g., the flag structure interrupts a beam of an optical sensor, which creates a pulse), a current rotational speed of the rotating gantry is determined. A clock frequency of a clock used to trigger sampling by the data acquisition system is set/adjusted based upon the current rotational speed and/or other factors, such as a number of views/samplings to acquire before a next flag structure is encountered by a sensor. The clock frequency establishes a sampling frequency (e.g., an integration period of a view between samplings) for the data acquisition system of the radiation imaging system for samples taken between an encounter with the flag structure and an encounter with a next flag structure (e.g., an encounter by the sensor with a different flag structure, an encounter by the sensor with the same flag structure, an encounter by a different sensor with the flag structure, or an encounter by the different sensor with a different flag structure).

A flag structure may comprise any type of physical structure or markers (e.g., an aperture, a fin, etc.) that are positioned along the partial arc segment. Because the one or more flag structures are positioned along the partial arc segment as opposed to an entire 360 degree structure, the one or more flag structures can be easily fabricated, installed, and maintained. In some embodiments, a plurality of flag structures can be individually positioned relative to a rotating gantry or a stationary support. In other embodiments, the plurality of flag structures can be manufactured into a single partial arc segment structure that can be positioned relative to or attached to the rotating gantry or the stationary support. The flag structures can be spaced along the partial arc segment at certain degree increments. In some embodiments, the respective flag structures may be spaced equidistance along the partial arc segment structure. In other embodiments, the flag structures may be spaced at non-uniform locations along the partial arc segment structure, and thus some sectors may represent a larger arc segment than other sectors. The length of the partial arc segment structure may be based upon a number of sensors and/or flag structures (e.g., a 180 degree arc segment structure may be used for 2 sensors, a 90 degree arc segment structure may be used for 4 sensors, a 45 degree arc segment structure may be used for 8 sensors, a 22.5 degree arc segment structure may be used for 16 sensors, etc.).

Any number of sensors and flag structures may be used. In some embodiments, the number of sensors and flag structures may be based upon a view timing precision. Each pulse generated by a sensor encountering a flag structure is an opportunity to determine a current rotational speed and to make an adjustment to the sampling frequency (e.g., if the rotating gantry is rotating faster than expected and thus less than a desired number of samples will be acquired within a revolution, the sampling frequency may be increased so that samples will be taken more frequently to compensate for the increased rotational speed). Thus, increasing the number of sensors and/or flag structures will result in more pulses that trigger the determination of the current rotational speed and the adjustment to the sampling frequency, thus providing improved view timing precision. Current rotational speed may be determined based upon an amount of time between pulses (e.g., between sensors encountering flags), distance between sensors and/or flag structures, etc.

For simplicity, throughout the remainder of the disclosure, the sensors will be described as being mounted to or attached to the rotating gantry while the flag structures are mounted to or attached to the stationary support. However, it may be appreciated that the positions of the sensor(s) and the flag structure(s) may be reversed. That is, it is contemplated that the flag structure(s) may be mounted to or attached to the rotating gantry and the sensor(s) will be described as being mounted to or attached to the stationary support. Moreover, some flag structures may be mounted to the rotating gantry while other flag structures may be mounted to the stationary support, and some sensors may be mounted to the stationary support while other sensors are mounted to the rotating gantry.

FIG. 1 illustrates an example radiation imaging system 100. In some embodiments, the radiation imaging system 100 is configured as a computed tomography (CT) system that rotates a radiation source 116 and a detector array 118 about an object 104 during an examination. Although, other types of three-dimension (3D) imaging systems, such as single-photon emission computed tomography (SPECT) systems are also contemplated.

The radiation imaging system 100 comprises an examination unit 102 configured to examine objects 104, such as baggage, a bone, tissue, etc. The examination unit 102 comprises a rotating gantry 106 and a stationary support 108 (e.g., which may encase and/or surround at least a portion of the rotating gantry 106 (e.g., as illustrated with an outer, stationary ring, surrounding an outside edge of an inner, rotating ring)). During an examination of an object 104, the object 104 is translated into and/or through an examination region 112 (e.g., a hollow bore in the rotating gantry 106) via a support article 110, such as a conveyor belt, roller assembly, etc. While the object 104 is situated within the examination region 112, the object 104 is exposed to radiation 120.

The rotating gantry 106 may surround a portion of the examination region 112 and may comprise the radiation source 116 (e.g., an ionizing radiation source such as an x-ray source or gamma-ray source) and the detector array 118. In some embodiments, the detector array 118 is mounted on a substantially diametrically opposite side of the rotating gantry 106 relative to the radiation source 116, and during an examination of the object 104, the rotating gantry 106 (e.g., including the radiation source 116 and detector array 118) is rotated about the object 104 by a rotor 114 (e.g., belt, drive shaft, chain, roller truck, etc.). Because the radiation source 116 and the detector array 118 are mounted to the rotating gantry 106, a relative position between the detector array 118 and the radiation source 116 may be substantially maintained during the rotation of the rotating gantry 106.

During the examination of the object 104, the radiation source 116 emits cone-beam or fan-beam shaped radiation 120 from a focal spot of the radiation source 116 (e.g., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multi-energy spectrums depending upon, among other things, whether the radiation imaging system 100 is configured as a single-energy system or a multi-energy (e.g., dual-energy) system.

As the emitted radiation 120 traverses the object 104, the radiation 120 may be attenuated differently by different aspects of the object 104. Because different aspects attenuate different percentages of the radiation 120, the number of photons detected by respective detector cells of the detector array 118 may vary. For example, more dense aspects of the object(s) 104, such as a bone or metal plate, may attenuate more of the radiation 120 (e.g., causing fewer photons to impinge a region of the detector array 118 shadowed by the more dense aspects) than less dense aspects, such as tissue or clothing.

Radiation detected by detector cells of the detector array 118 may be directly or indirectly converted into electrical charge, which may accumulate within the detector cell. Moreover, the detector array 118 or detector cells may or may not be configured to discriminate detected radiation on the basis of the energy of the detected radiation. For example, the detector cells may comprise a stacked arrangement (e.g., sometimes called a sandwich-type detector cell) configured to discriminate between two or more energy spectra. As another example, the detector array 118 may comprise a filter that overlies at least some of the detector cells. The filter may cause underlying detector cells to detect a different energy range than the energy range detected by detector cells that do not underlie the filter.

The charge that has accumulated during an integration period may be readout by a data acquisition system 122 during an integration to generate an analog signal indicative of the incoming radiation photon flux rate at respective detector cells. The data acquisition system 122 may also be configured to convert the analog signals into digital signals. These digitals signals are typically in projection space and are, at times, referred to as projections or projection data.

The data acquisition system 122 is coupled to a triggering system 134 configured to initiate integrations at the data acquisition system 122 according to sampling frequency established by a clock frequency of a clock that is adjusted dynamically when a sensor encounters a flag structure. Flag structures may be disposed on or positioned relative to the stationary support 108. The flag structures may be formed according to a partial arc segment as opposed to a full 360 degree structure (e.g., an arc structure that is less than a full 360 degree circle). In some embodiments, the flag structures may include apertures, fins, or magnets disposed on the stationary support 108 adjacent an airgap between the rotating gantry 106 and the stationary support 108. The triggering system 134 may use the flag structures to trigger a number of samplings (e.g., integrations) between a sensor encountering a flag structure and a next encounter of a sensor with a flag structure (e.g., the sensor encountering a different flag structure, the sensor encountering the flag structure again, a second sensor encountering the same flag structure, the second sensor encountering a different flag structure, etc.), to determine a location of the rotating gantry 106 relative to the stationary support 108, and/or to determine a rotational period of the rotating gantry 106. The triggering system 134 may also comprise an optical sensor, magnetic sensor, a capacitive sensor, an inductive proximity sensor, or other sensor disposed on the rotating gantry 106. A sensor is configured to identify a flag structure when the sensor encounters the flag structure. The triggering system 134 may also comprise a timing element configured to trigger (e.g., initiate) integrations at the data acquisition system 122 according to the sampling frequency. As will be described in more detail below, the sampling frequency may be adjusted dynamically during a revolution based upon a current rotational speed of the rotating gantry 106 and/or other data such as a number of samples to acquire before the next encounter of a sensor with a flag structure or a number of samples to acquire during a next sampling interval. Moreover, the data acquisition system 122 or other components of the radiation imaging system 100, such as a controller 132, may use the identification of flag structures by the sensors to determine or verify a rotational positioning of the rotating gantry 106 relative to the stationary support 108.

In some embodiments, the triggering system 134 is coupled to a terminal 126 (e.g., a workstation or computer) and information may be exchanged between the triggering system 134 and the terminal 126. In some embodiments, information transmitted to the triggering system 134 from the terminal 126 may be used to determine a desired number of samplings (e.g., integrations, views, etc.) per revolution. For example, a user 130 may specify, at the terminal 126, a desired image resolution or other image parameter for images produced by the image generator 124 and, based upon this user specification, the triggering system 134 may determine a desired number of integrations per revolution. As still another example, the terminal 126 may, via user input or programmatically, determine the type of object under examination, and the triggering system 134 may determine the desired number of integrations per revolution based upon the type of object under examination.

The projections generated by the data acquisition system 122 may be transmitted to an image generator 124 operably coupled to the data acquisition system 122. The image generator 124 is configured to convert at least some of the data from projection space to image space using suitable analytical, iterative, and/or other reconstruction techniques (e.g., tomosynthesis reconstruction, back-projection, iterative reconstruction, etc.) and/or to compile at least some of the data to generate two-dimensional and/or three-dimensional images of the object 104.

The terminal 126 is operably coupled to the image generator 124 and is configured to receive the image(s), which can be displayed on a monitor 128 to the user 130 (e.g., security personnel, medical personnel, etc.). In this way, the user 130 can inspect the image(s) to identify areas of interest within the object(s) 104. The terminal 126 can also be configured to receive user input that can direct operations of the examination unit 102 (e.g., a speed of a conveyor belt, activation of the radiation source(s) 116, etc.).

In the example radiation imaging system 100, a controller 132 is operably coupled to the terminal 126. The controller 132 may be configured to control operations of the examination unit 102, for example. By way of example, in some embodiments, the controller 132 is configured to receive information from the terminal 126 (e.g., a command to adjust a speed of a conveyor belt, a command to adjust a desired rotational speed of the rotating gantry 106, etc.).

It may be appreciated that components of the radiation imaging system 100 described above are merely example components and the arrangement of such components is merely an example arrangement. Such components and/or arrangements are not intended to be interpreted in a limiting manner, such as necessarily specifying the location, inclusion, and/or relative position of the components. By way of example, in some embodiments, the data acquisition system 122 is part of the detector array 118 and/or is located on a rotating gantry 106 of the radiation imaging system 100.

Figure 2:
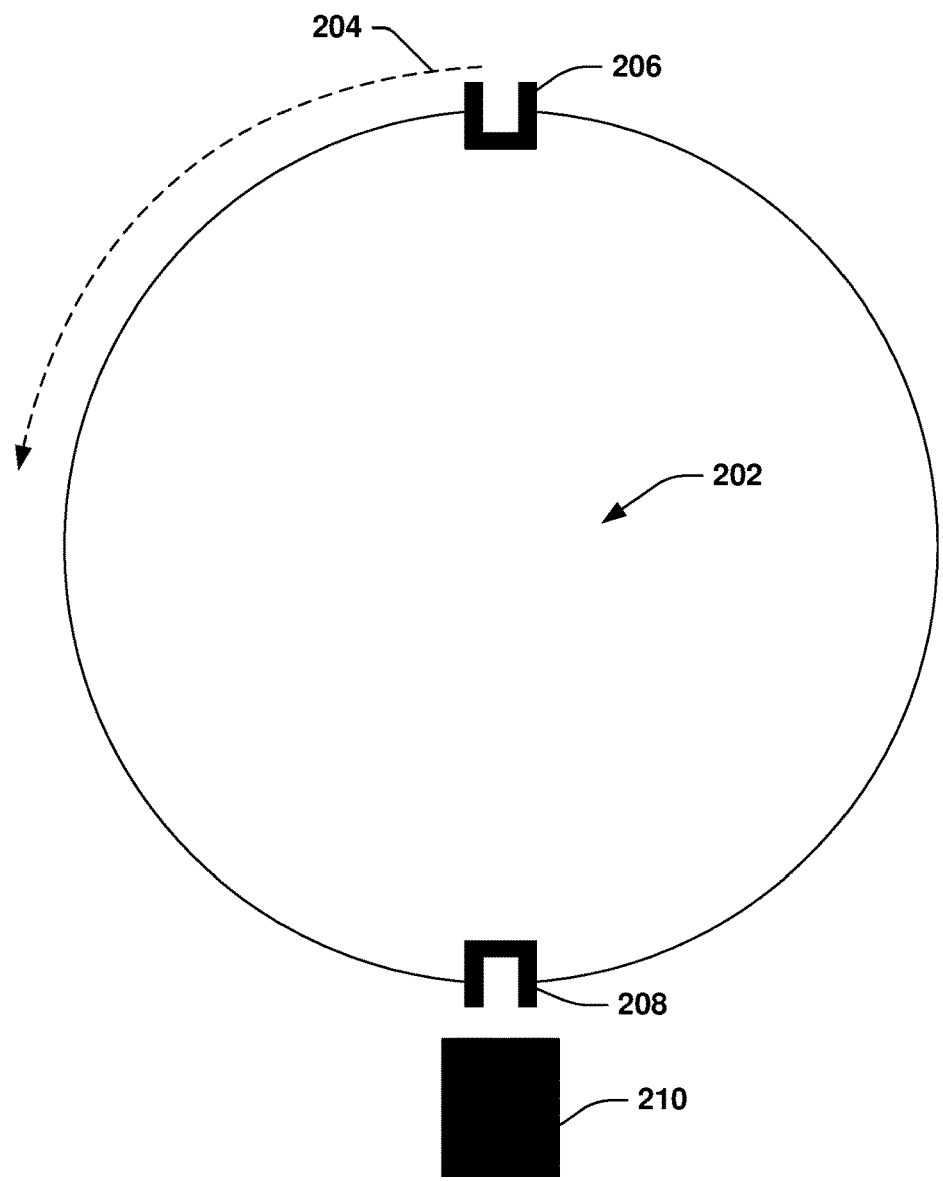
FIG. 2 illustrates example technique for setting a sampling frequency for a radiation imaging system using two sensors and a flag structure.
Figure 2:
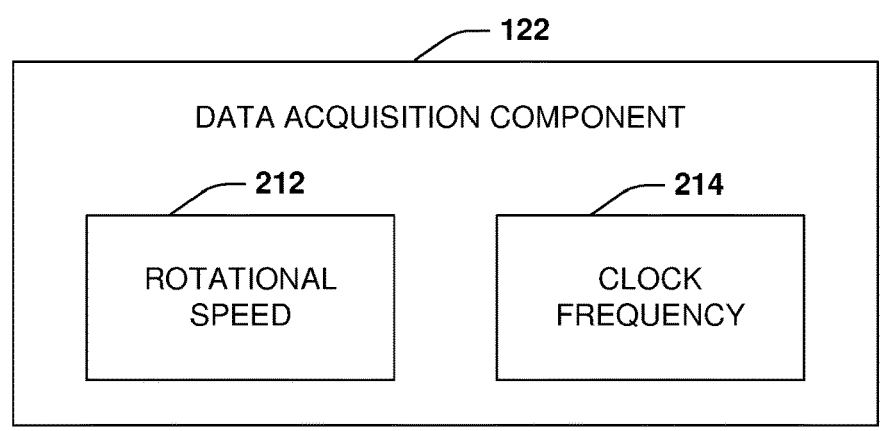

FIG. 2 provides an example technique for setting a sampling frequency for the data acquisition system 122. The sampling frequency may correspond to a frequency at which samples are captured by the data acquisition system 122. For example, the sampling frequency corresponds to a triggering rate of obtaining samplings (e.g., reading charge accumulated within transistors of the detector array 118). If a particular number of samples (e.g., views) are to be acquired during a revolution 204 of a rotating gantry 202, then the sampling frequency can be adjusted dynamically based upon current rotational speeds determined for the rotating gantry when sensors encounter flag structures.

In some embodiments, a first sensor 206, a second sensor 208, and/or other sensors (e.g., optical sensors, magnetic sensors, etc.) are disposed on a rotating gantry 202 (e.g., 106 in FIG. 1). A first flag structure 210 and/or other flag structures may be positioned relative to a stationary support (e.g., 108 in FIG. 1). During a revolution 204 of the rotating gantry 202, the first sensor 206 and the second sensor 208 will individually encounter (e.g., traverse, detect, etc.) the first flag structure 210. In some embodiments, the second sensor 208 encounters the first flag structure 210, such as where an optical beam of the second sensor 208 is broken/blocked by the first flag structure 210 or where a magnetic field is detected from magnetic material of the first flag structure 210 by the second sensor 208. The encounter may result in a pulse comprising a rising edge when the second sensor 208 first encounters the first flag structure 210 (e.g., when the optical beam is first broken) and a falling edge when the second sensor 208 finishes encountering the first flag structure 210 (e.g., when the optical beam stops being broken). It may be appreciated that while reference is made to a magnetic-based sensor, other types of sensors are also contemplated. For example, sensors 206, 208, may be electrical-field based sensors (e.g., capacitive or inductive proximity sensors) or light-based sensors (e.g., opto-sensors). Moreover, the types of flag structures 210 that are selected may be a function of the type of sensors that are selected.

When the second sensor 208 encounters the first flag structure 210, a current rotational speed 212 of the rotating gantry 202 is determined. In some embodiments, the current rotational speed 212 can be determined based upon an amount of time that has lapsed since a last encounter with the first flag structure 210, such as when the first sensor 206 last encountered the first flag structure 210. As another example, the current rotational speed 212 can be determined using the rising edge and the falling edge of the pulse (since the distance between a first edge of first flag structure 210 that triggered the rising edge and a second edge of the first flag structure 210 that triggered the falling edge is known).

Various factors can affect the current rotational speed 212 of the rotating gantry 202, and thus the current rotational speed 212 may not be constant. Such variances in the current rotational speed 212 can adversely impact the ability to capture a desired number of views during a revolution 204 of the rotating gantry 202. If the rotating gantry 202's speed increases while the frequency of sampling remains constant, then a number of views captured will be less than expected. Accordingly, the sampling frequency may be adjusted dynamically during rotation of the rotating gantry 202 during each pulse.

In some embodiments, when the second sensor 208 encounters the first flag structure 210 and the current rotational speed 212 is determined, a clock frequency 214 of a clock is set based upon the current rotational speed 212 and/or other data such as a desired number of views to capture during a next sampling period (e.g., a number of samplings to perform before a next encounter of a sensor with a flag structure such as the first sensor 206 encountering the first flag structure 210). The clock frequency establishes a sampling frequency for the data acquisition system 122 for samples taken between the second sensor 208 encountering the first flag structure 210 and the first sensor 206 encountering the first flag structure 210 (e.g., a next encounter of a flag structure by a sensor). In some embodiments, if the current rotational speed 212 indicates that the rotating gantry 202 is rotating faster than expected or faster than previously measured, then the sampling frequency may be increased so that a target number of desired views per revolution is still obtainable. Otherwise, the rotating gantry 202 may rotate too quickly for all remaining views/samples to be captured.

In this way, the data acquisition system 122 will sample detector cells according to the sampling frequency set by the clock until the first sensor 206 subsequently encounters the first flag structure 210. When the first flag structure 210 is encountered by the first sensor 206, a new current rotational speed is determined and used to set the clock frequency of the clock for adjusting the sampling frequency.

Figure 3:
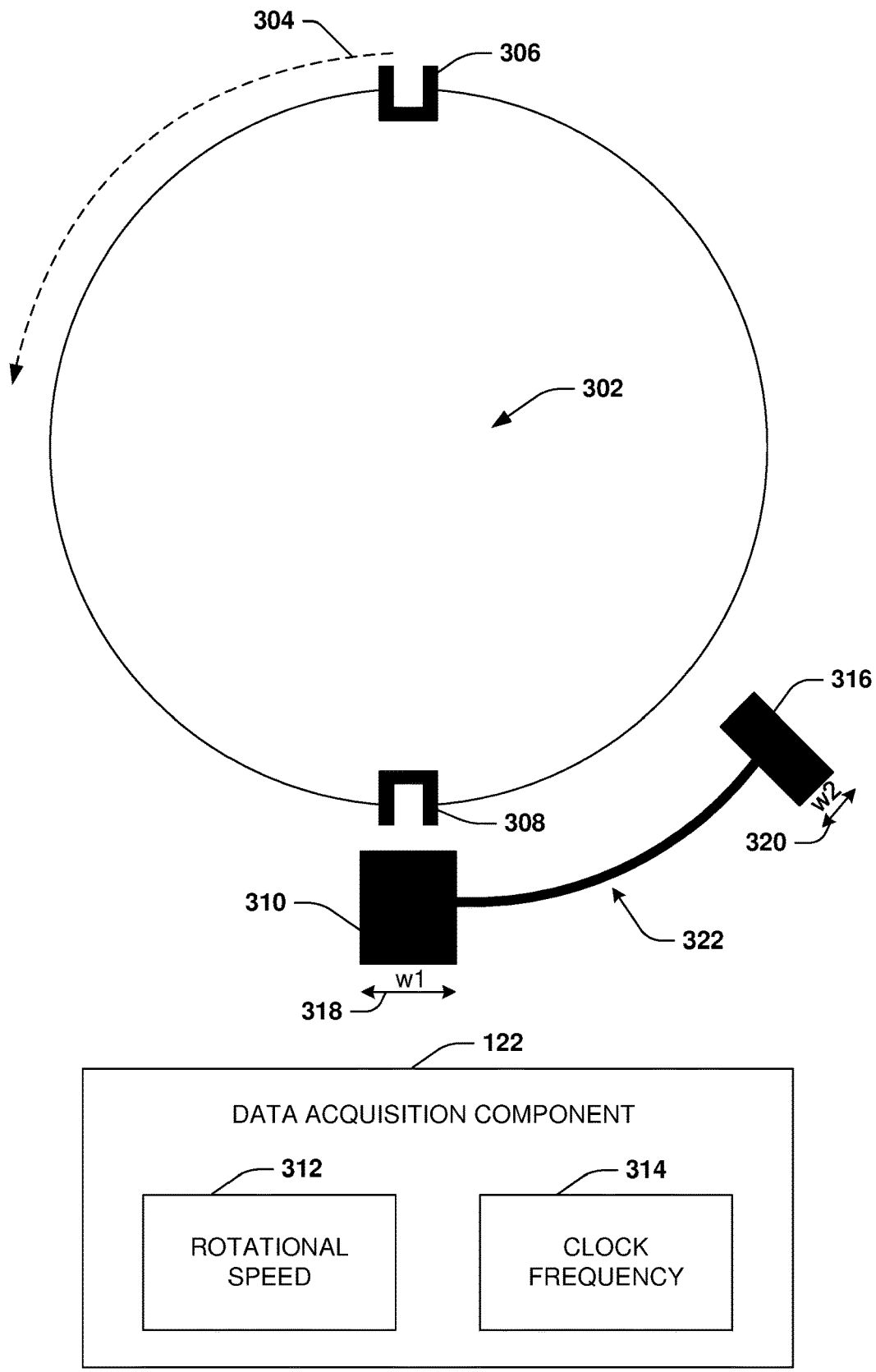
FIG. 3 illustrates example technique for setting a sampling frequency for a radiation imaging system using two sensors and two flag structures, wherein a first flag structure has a different size than a second flag structure.

FIG. 3 provides an example technique for setting a sampling frequency for the data acquisition system 122. The sampling frequency may correspond to a frequency at which samples (e.g., views) are captured by the data acquisition system 122. In some embodiments, a first sensor 306, a second sensor 308, and/or other sensors are disposed on a rotating gantry 302 (e.g., 106 in FIG. 1) configured to rotate 304. A first flag structure 310, a second flag structure 316, and/or other flag structures may be positioned relative to a stationary support (e.g., 108 in FIG. 1). The first flag structure 310 and the second flag structure 316 may be formed according to a partial arc segment 322 (e.g., disposed along a structure that is less than a full 360 degree structure, such as a 45 degree structure). In some embodiments, the first flag structure 310 is positioned 45 degrees or any other angular distance from the second flag structure 316. In some embodiments where there are 3 flag structures, each flag structure may be positioned along a 90 degree arc segment with 30 degree spacing between each flag structure. In some embodiments, a flag structure, such as the first flag structure 310, is designated as a home flag structure. Thus, when a sensor encounters the home flag structure and then the same sensor subsequently encounters the home flag structure, a determination can be made that a full revolution of the rotating gantry 302 has been performed with respect to that sensor.

During a revolution of the rotating gantry 302, the first sensor 306 and the second sensor 308 will individually encounter (e.g., traverse, detect, etc.) the first flag structure 310 and the second flag structure 316. In some embodiments, the second sensor 308 encounters the first flag structure 310 and a first pulse is generated (e.g., the first pulse may correspond to an amount of time an optical beam of the second sensor 308 is broken/blocked by the first flag structure 310 or an amount of time the second sensor 308 and the first flag structure 310 form a capacitive link, for example, and thus a width of the pulse may correspond to a width of the first flag structure 310). The second sensor 308 next encounters the second flag structure 316 and a second pulse is generated. The first sensor 306 next encounters the first flag structure 310 and a third pulse is generated. Finally the first sensor 306 encounters the second flag structure 316 and a fourth pulse is generated.

At each pulse, a current rotational speed 312 of the rotating gantry 302 is determined. A clock frequency 314 of a clock is set based upon the current rotational speed 312 and/or other data (e.g., a number of samples/views to still obtain before a full revolution is performed or to obtain during a next sampling segment period such as a time until a next pulse occurs) in order to establish a sampling frequency used for sampling detector cells until a next pulse occurs (e.g., a next encounter of a sensor with a flag structure). In some embodiments, the current rotational speed 312 is determined upon a time that has lapsed between a rising edge of a first pulse and a rising edge of a next pulse. The clock frequency 314 may be set (e.g., committed) thereafter such as upon detection of a falling edge of the next pulse. Thus, the frequency at which views are captured for the segment between a first flag structure 310 and a second flag structure 316 is set upon the falling edge of the pulse created responsive to the second sensor 308 encountering a sidewall of the first flag structure 310 nearest the second flag structure 316.

A width of a pulse may be dependent upon a width of a flag structure. The wider the flag structure, the longer a sensor encounters the flag structure thus resulting in a longer pulse width. In some embodiments, flag structures may have the same width. In other embodiments, flag structures may have different widths. For example, the first flag structure 310 may have a first width 318. The second flag structure 316 may have a second width 320 different than the first width 318. For example, the first width 318 may be wider than the second width 320. Thus, a first pulse of a sensor encountering the first flag structure 310 will result in a wider pulse than a second pulse of the sensor encountering the second flag structure 316. In this way, flag structures can be identified and differentiated between based upon widths of pulses that they produce (e.g., further enabling the radiation imaging system 100 to determine/verify the rotating gantry 106 rotational position relative to the stationary support 108). Accordingly, a current location of the rotating gantry 302 may be determined based upon a width of a pulse that was just encountered. For example, the rotating gantry 302 may have a rotational orientation such that the second sensor 308 is at a position facing the first flag structure 310 based upon a detected pulse width corresponding to the first width 318 of the first flag structure 310.

Figure 4:
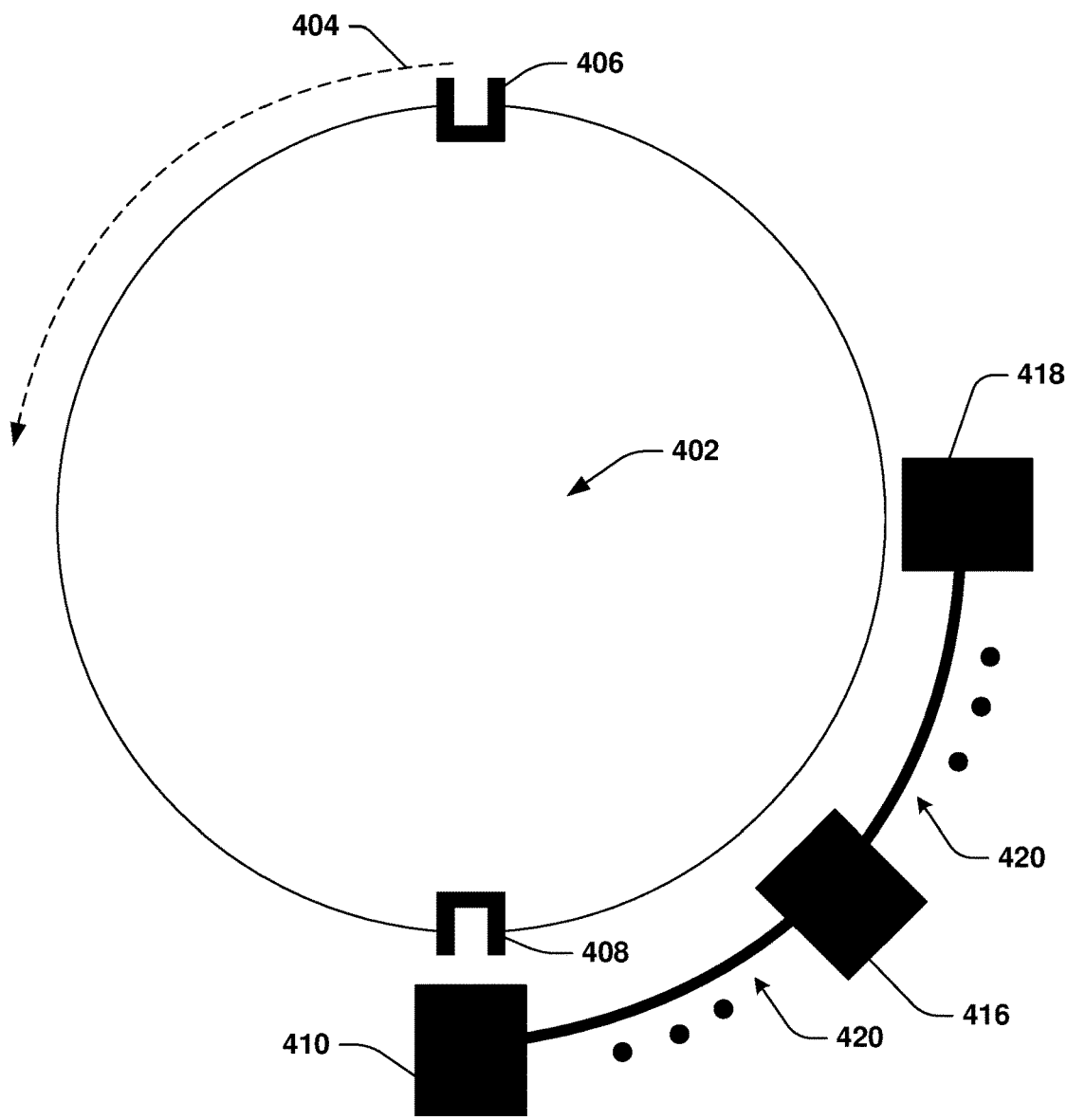
FIG. 4 illustrates example technique for setting a sampling frequency for a radiation imaging system using two sensors and a plurality of flag structures.

FIG. 4 provides an example technique for setting a sampling frequency for the data acquisition system 122. The sampling frequency may correspond to a frequency at which samples (e.g., views) are captured by the data acquisition system 122. In some embodiments, a first sensor 406, a second sensor 408, and/or other sensors (e.g., optical sensors, magnetic sensors, etc.) are disposed on a rotating gantry 402 (e.g., 106 in FIG. 1) configured to rotate 404.

A first flag structure 410, a second flag structure 416, a third flag structure 418, and/or other flag structures may be positioned relative to a stationary support (e.g., 108 in FIG. 1). The first flag structure 410, the second flag structure 416, and/or the third flag structure 418 may be formed according to a partial arc segment 420 (e.g., disposed along a structure that is less than a full 360 degree structure, such as 90 degree structure). In some embodiments, the first flag structure 410 is positioned 45 degrees or any other angular distance from the second flag structure 416 and the third flag structure 418 is positioned 45 degrees or any other angular distance from the second flag structure 416. In some embodiments, a flag structure, such as the first flag structure 410, is designated as a home flag structure. Thus, when a sensor encounters the home flag structure and then the same sensor subsequently encounters the home flag structure, a determination can be made that a full revolution of the rotating gantry 402 has been performed with respect to that sensor.

During a revolution of the rotating gantry 402, the first sensor 406 and the second sensor 408 will individually encounter (e.g., traverse, detect, etc.) the first flag structure 410, the second flag structure 416, and the third flag structure 418. In some embodiments, the second sensor 408 encounters the first flag structure 410 and a first pulse is generated. The second sensor 408 next encounters the second flag structure 416 and a second pulse is generated. The second sensor 408 next encounters the third flag structure 418 and a third pulse is generated. The first sensor 406 next encounters the first flag structure 410 and a fourth pulse is generated. The first sensor 406 next encounters the second flag structure 416 and a fifth pulse is generated. Finally the first sensor 406 encounters the third flag structure 418 and a sixth pulse is generated.

At each pulse, a current rotational speed 412 of the rotating gantry 402 is determined, and a clock frequency 414 of a clock is set based upon the current rotational speed 412 and/or other data (e.g., a number of views to obtain before a next pulse occurs or a full revolution is complete) in order to establish a sampling frequency used for sampling detector cells until a next pulse occurs (e.g., a next encounter of a sensor with a flag structure). In some embodiments, the current rotational speed 412 is determined upon detection of a rising edge of a pulse. The clock frequency 414 may be set thereafter such as upon detection of a falling edge of the pulse.

Figure 5A:
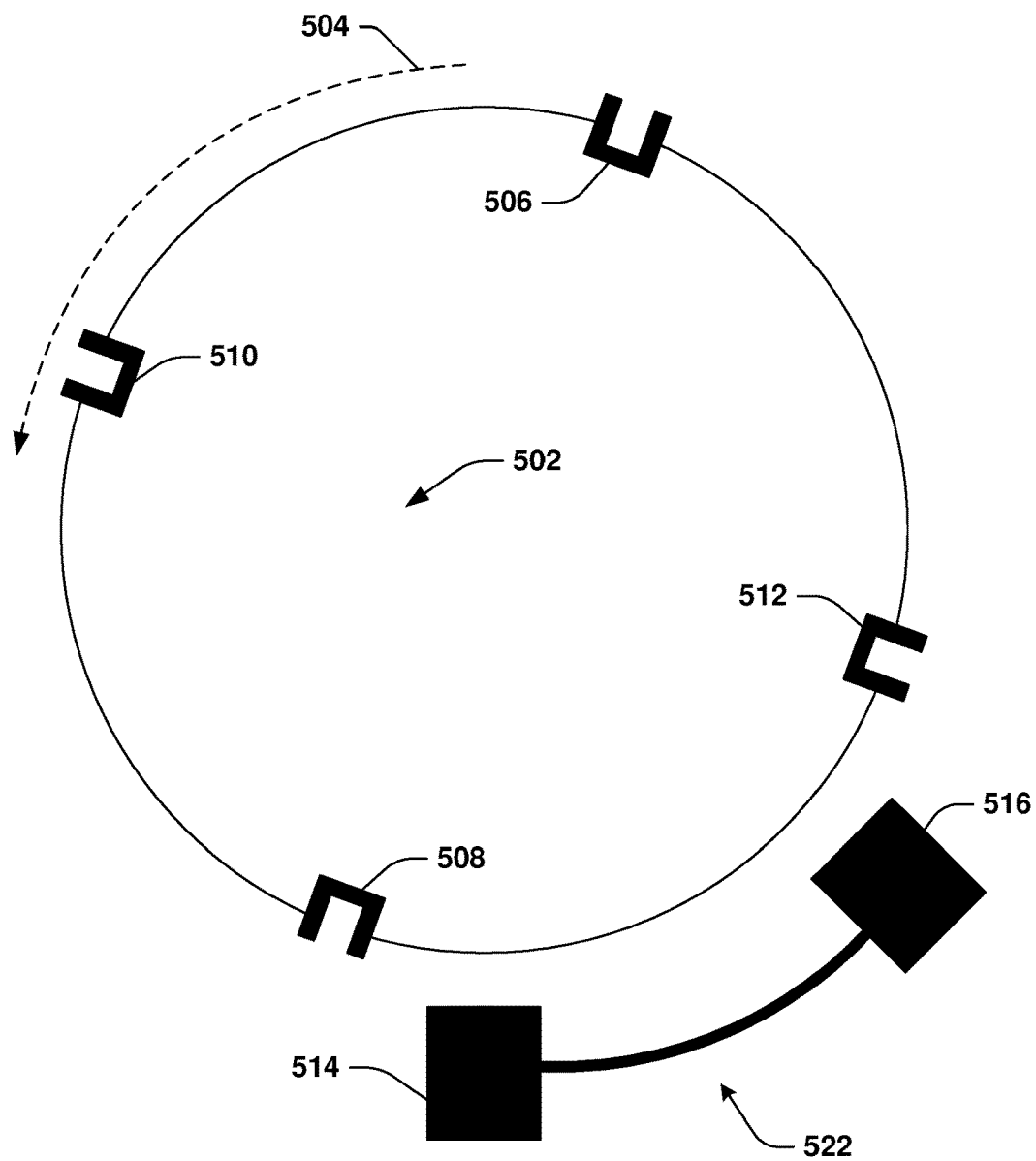
FIG. 5A illustrates example technique for setting a sampling frequency for a radiation imaging system.
Figure 5A:
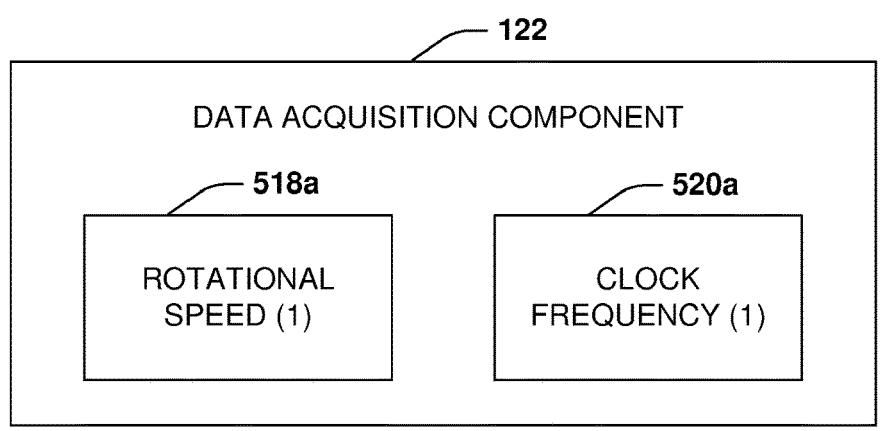

FIGS. 5A-5G provide an example technique for setting a sampling frequency for the data acquisition system 122. The sampling frequency may correspond to a frequency at which samples are captured by the data acquisition system 122. FIG. 5A illustrates a first sensor 506, a second sensor 508, a third sensor 510, and a fourth sensor 512 that are disposed on rotating gantry 502 (e.g., 106 in FIG. 1) configured to rotate 504. The rotating gantry 502 is depicted at a first position.

A first flag structure 514, a second flag structure 516, and/or any other number of flag structures may be positioned relative to a stationary support (e.g., 108 in FIG. 1). The first flag structure 514 and the second flag structure 516 may be formed according to a partial arc segment 522 (e.g., positioned along a structure that is less than a full 360 degree structure, such as 45 degree structure). In some embodiments, the first flag structure 514 is positioned 45 degrees or any other angular distance from the second flag structure 516. In some embodiments, a flag structure, such as the first flag structure 514, is designated as a home flag structure. Thus, when a sensor encounters the home flag structure and then the same sensor subsequently encounters the home flag structure, a determination can be made that a full revolution of the rotating gantry 502 has been performed with respect to that sensor. A first current rotational speed 518*a* may have been determined when the fourth sensor 512 encountered the second flag structure 516. A first clock frequency 520*a* may have been set for a clock to establish a first sampling frequency used to sample detector cells (e.g., capture samples/views) until a next encounter of a flag structure by a sensor (e.g., the second sensor 508 encountering the first flag structure 514 as further described in relation to FIG. 5B).

Figure 5B:
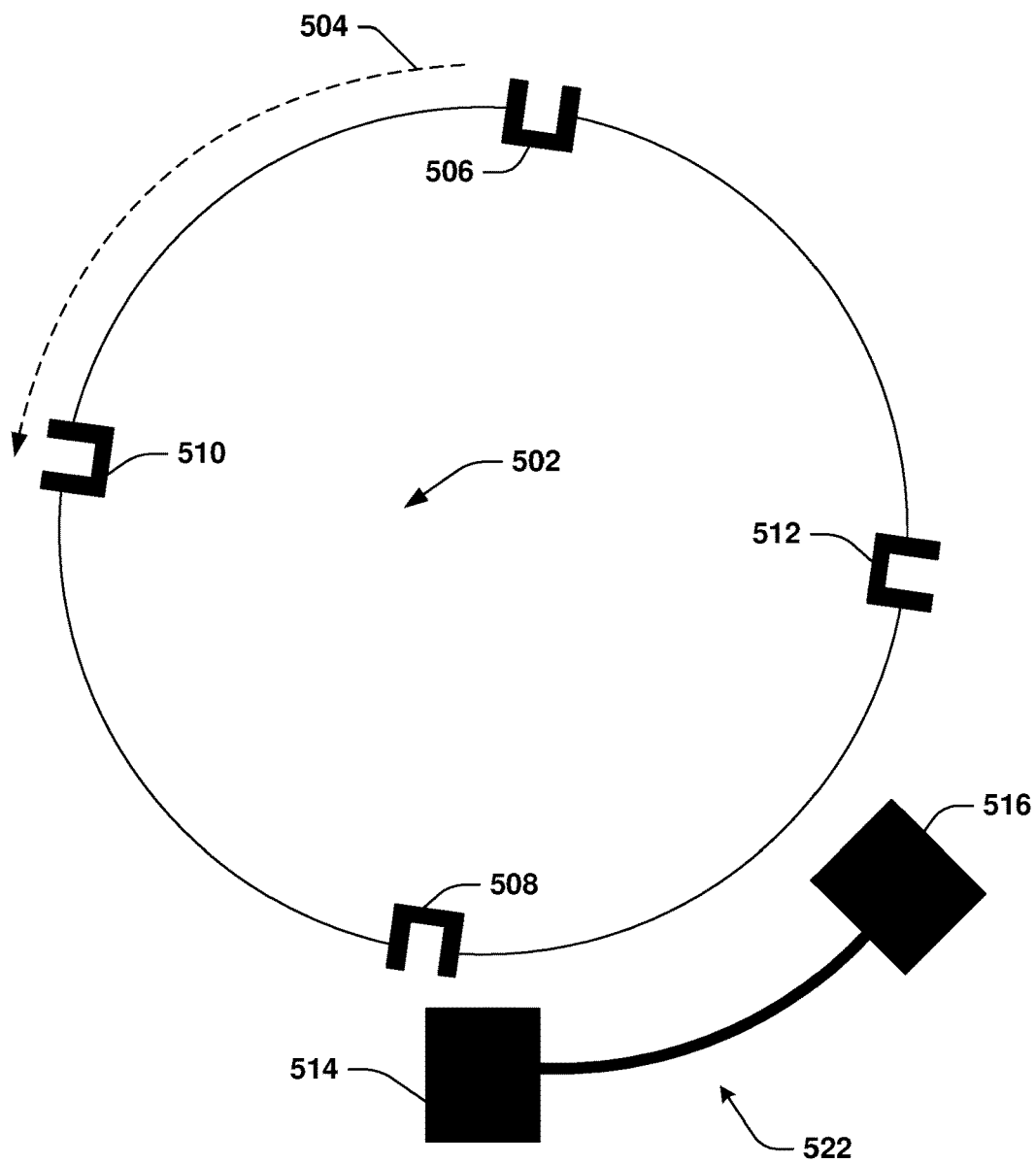
FIG. 5B illustrates example technique for setting a sampling frequency for a radiation imaging system, where a current rotational speed is determined.
Figure 5B:
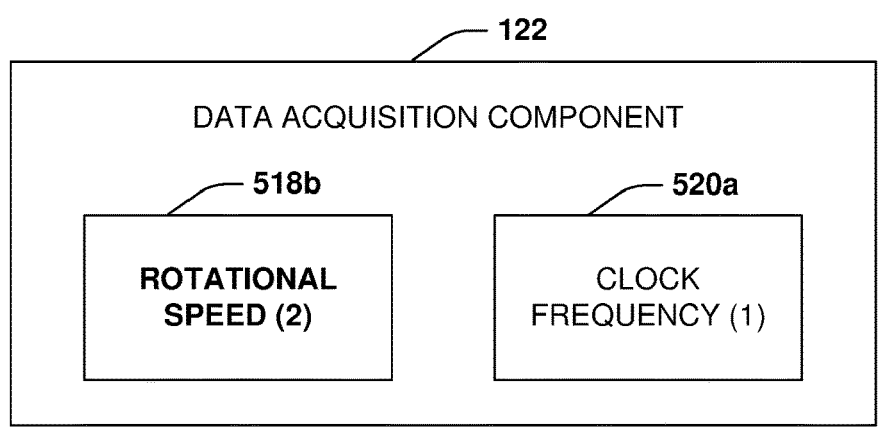

FIG. 5B illustrates the rotating gantry 502 at a second position after a certain amount of rotation 504. The second sensor 508 encounters the first flag structure 514 (e.g., an instance at which an optical beam from the second sensor 508 is interrupted/broken by the first flag structure 514), which is detected as a rising edge of a first pulse. Accordingly, a second current rotational speed 518*b* is determined.

Figure 5C:
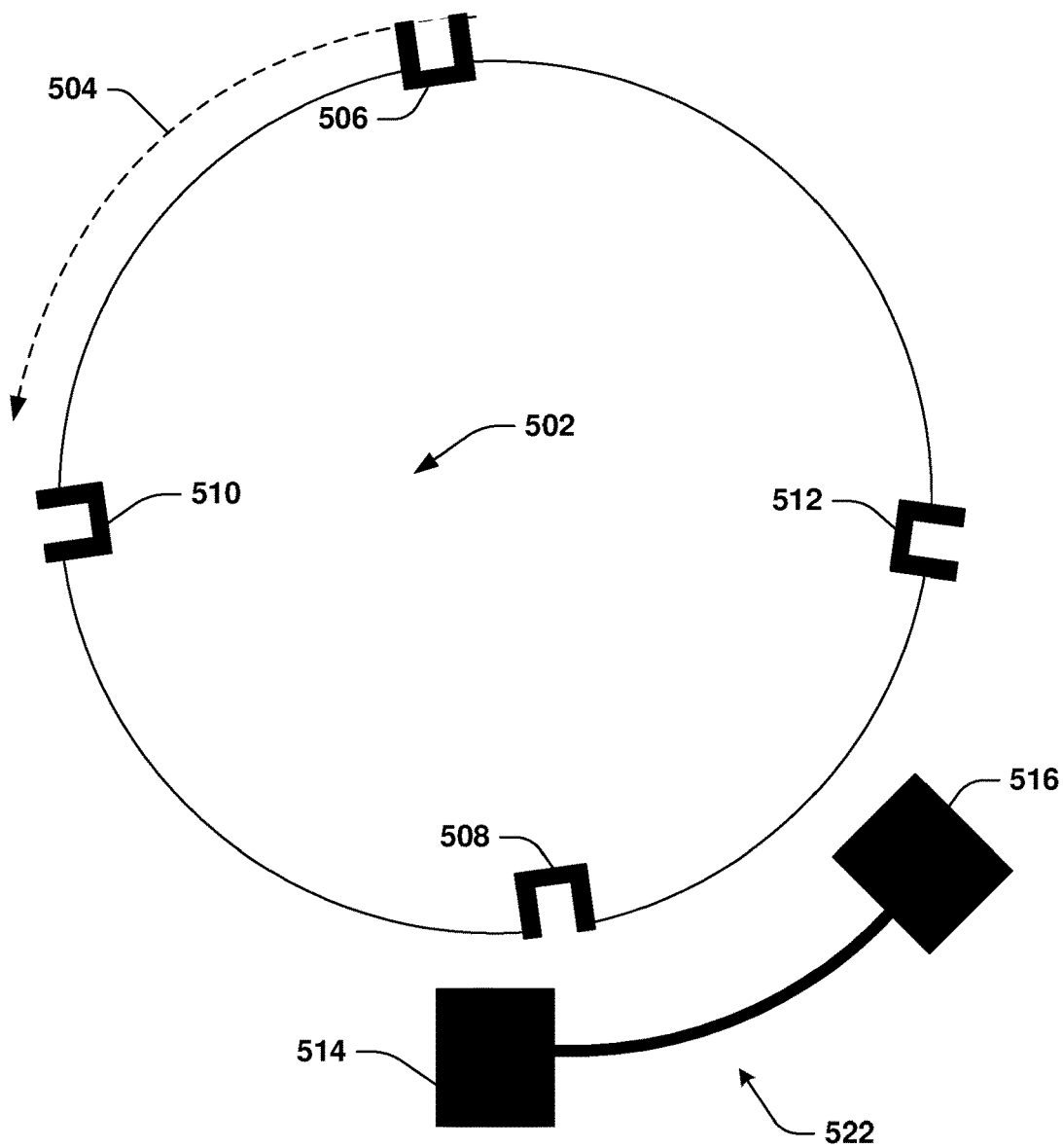
FIG. 5C illustrates example technique for setting a sampling frequency for a radiation imaging system, where a clock frequency is set.
Figure 5C:
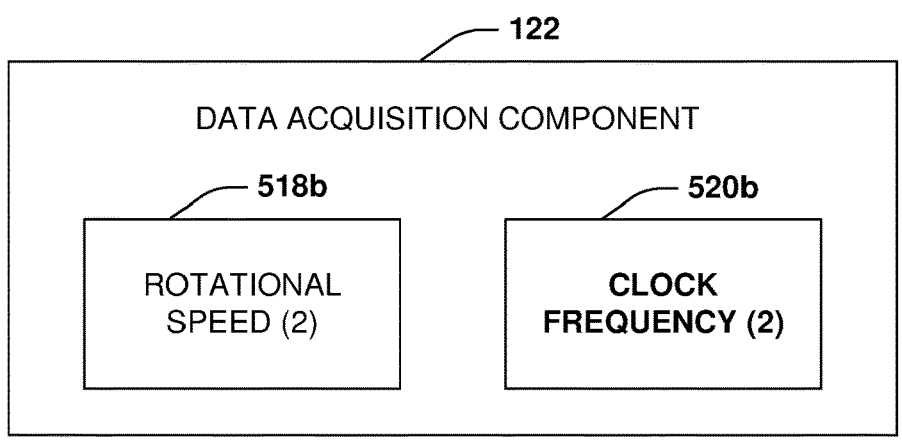

FIG. 5C illustrates the rotating gantry 502 at a third position after a certain amount of rotation 504. The second sensor 508 finishes encountering the first flag structure 514 (e.g., an instance at which the optical beam from the second sensor 508 is no longer interrupted/broken by the first flag structure 514), which is detected as a falling edge of the first pulse. Accordingly, a second clock frequency 520*b* is set for the clock based upon the second current rotational speed 518*b* and/or other data such as a desired number of views remaining to capture. The second clock frequency 520*b* establishes a second sampling frequency used to sample detector cells (e.g., capture samples/views) until a next encounter of a flag structure by a sensor (e.g., the second sensor 508 encountering the second flag structure 516 as further described in relation to FIG. 5D). In some embodiments, if the second current rotational speed 518*b* indicates an increase in rotational speed, then the second clock frequency 520*b* may be set as an increased frequency value so that a desired number of views can still be captured. If the second current rotational speed 518*b* indicates a decrease in rotational speed, then the second clock frequency 520*b* may be set as a decreased frequency value so that unnecessary views beyond the desired number of views are not captured.

Figure 5D:
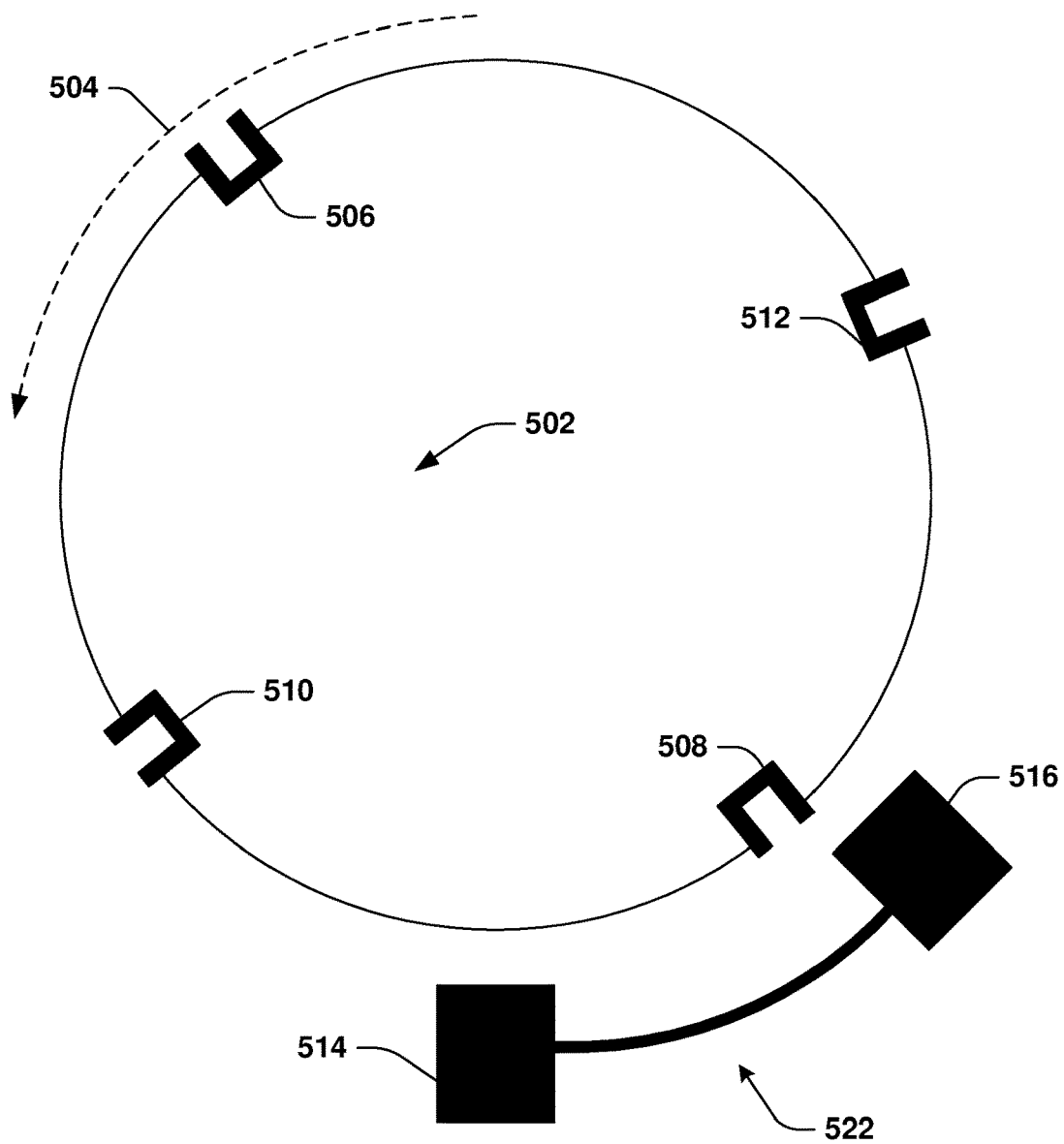
FIG. 5D illustrates example technique for setting a sampling frequency for a radiation imaging system, where a current rotational speed is determined.
Figure 5D:
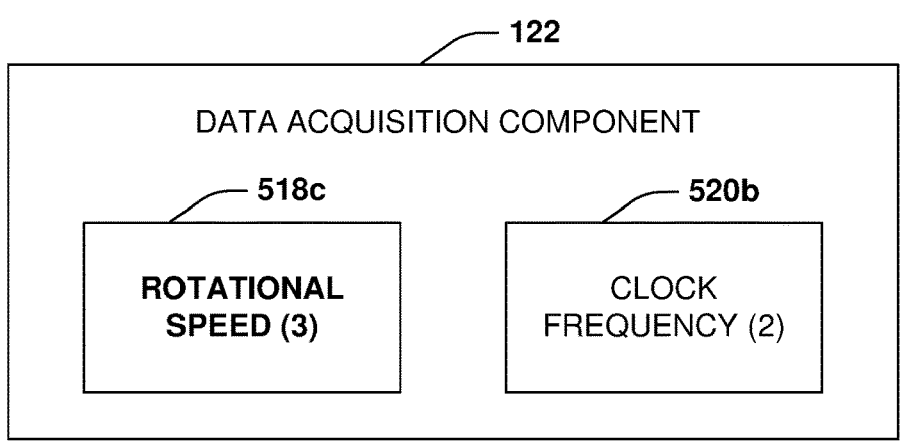

FIG. 5D illustrates the rotating gantry 502 at a fourth position after a certain amount of rotation 504. The second sensor 508 encounters the second flag structure 516 (e.g., an instance at which the optical beam from the second sensor 508 is interrupted/broken by the second flag structure 516), which is detected as a rising edge of a second pulse. Accordingly, a third current rotational speed 518*c* is determined.

Figure 5E:
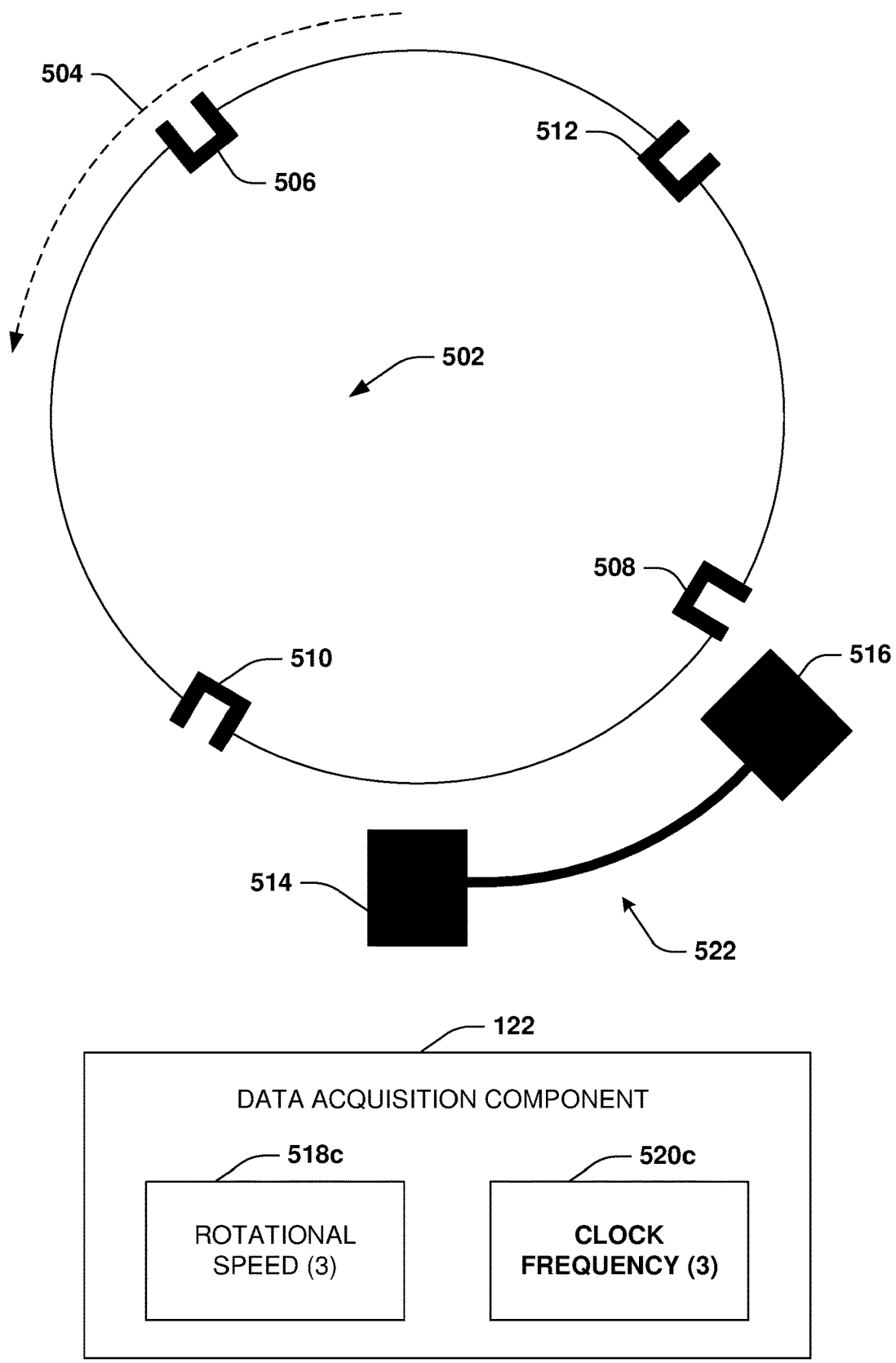
FIG. 5E illustrates example technique for setting a sampling frequency for a radiation imaging system, where a clock frequency is set.

FIG. 5E illustrates the rotating gantry 502 at a fifth position after a certain amount of rotation 504. The second sensor 508 finishes encountering the second flag structure 516 (e.g., an instance at which the optical beam from the second sensor 508 is no longer interrupted/broken by the second flag structure 516), which is detected as a falling edge of the second pulse. Accordingly, a third clock frequency 520*c* is set for the clock based upon the third current rotational speed 518*c* and/or other data such as a desired number of views remaining to capture. The third clock frequency 520*c* establishes a third sampling frequency used to sample detector cells (e.g., capture samples/views) until a next encounter of a flag structure by a sensor (e.g., the third sensor 510 encountering the first flag structure 514 as further described in relation to FIG. 5F). In some embodiments, if the third current rotational speed 518c indicates an increase in rotational speed, then the third clock frequency 520c may be set as an increased frequency value so that a desired number of views can still be captured. If the third current rotational speed 518c indicates a decrease in rotational speed, then the third clock frequency 520c may be set as a decreased frequency value so that unnecessary views beyond the desired number of views are not captured.

Figure 5F:
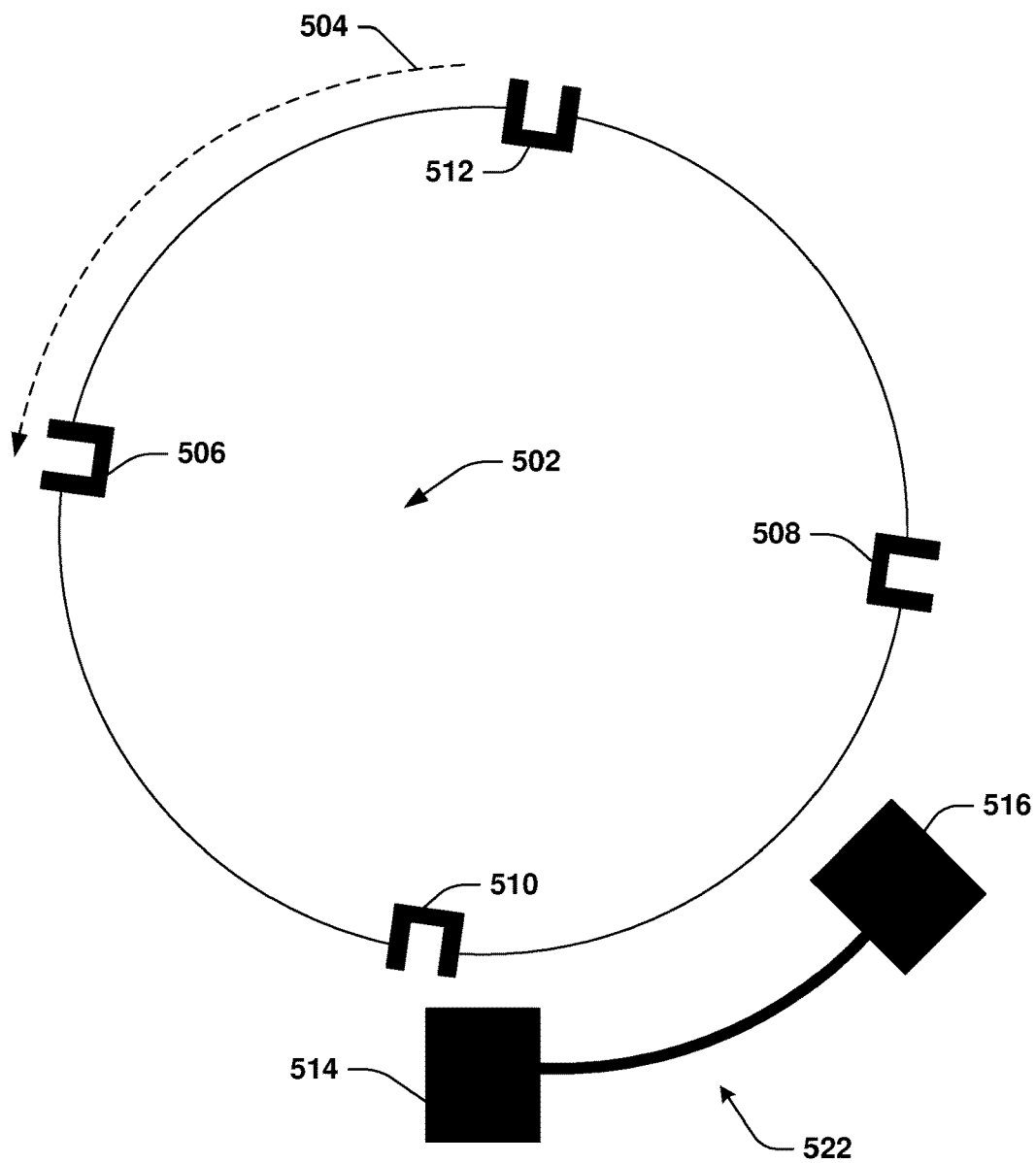
FIG. 5F illustrates example technique for setting a sampling frequency for a radiation imaging system, where a current rotational speed is determined.
Figure 5F:
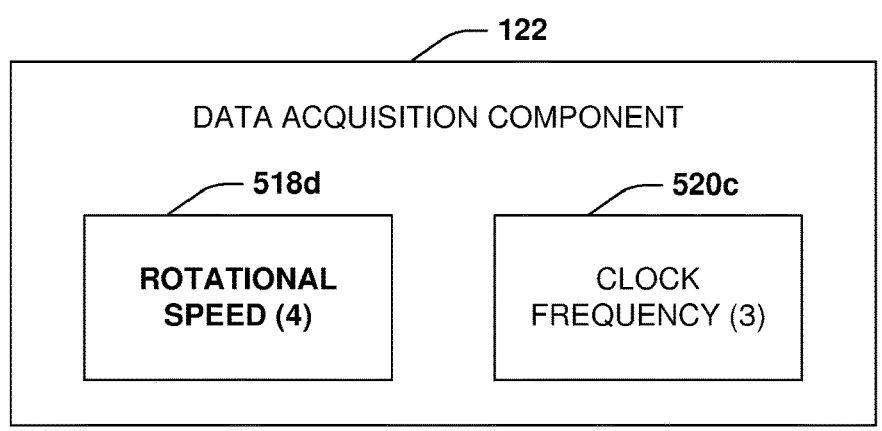

FIG. 5F illustrates the rotating gantry 502 at a sixth position after a certain amount of rotation 504. The third sensor 510 encounters the first flag structure 514 (e.g., an instance at which an optical beam from the third sensor 510 is interrupted/broken by the first flag structure 514), which is detected as a rising edge of a third pulse. Accordingly, a fourth current rotational speed 518d is determined.

Figure 5G:
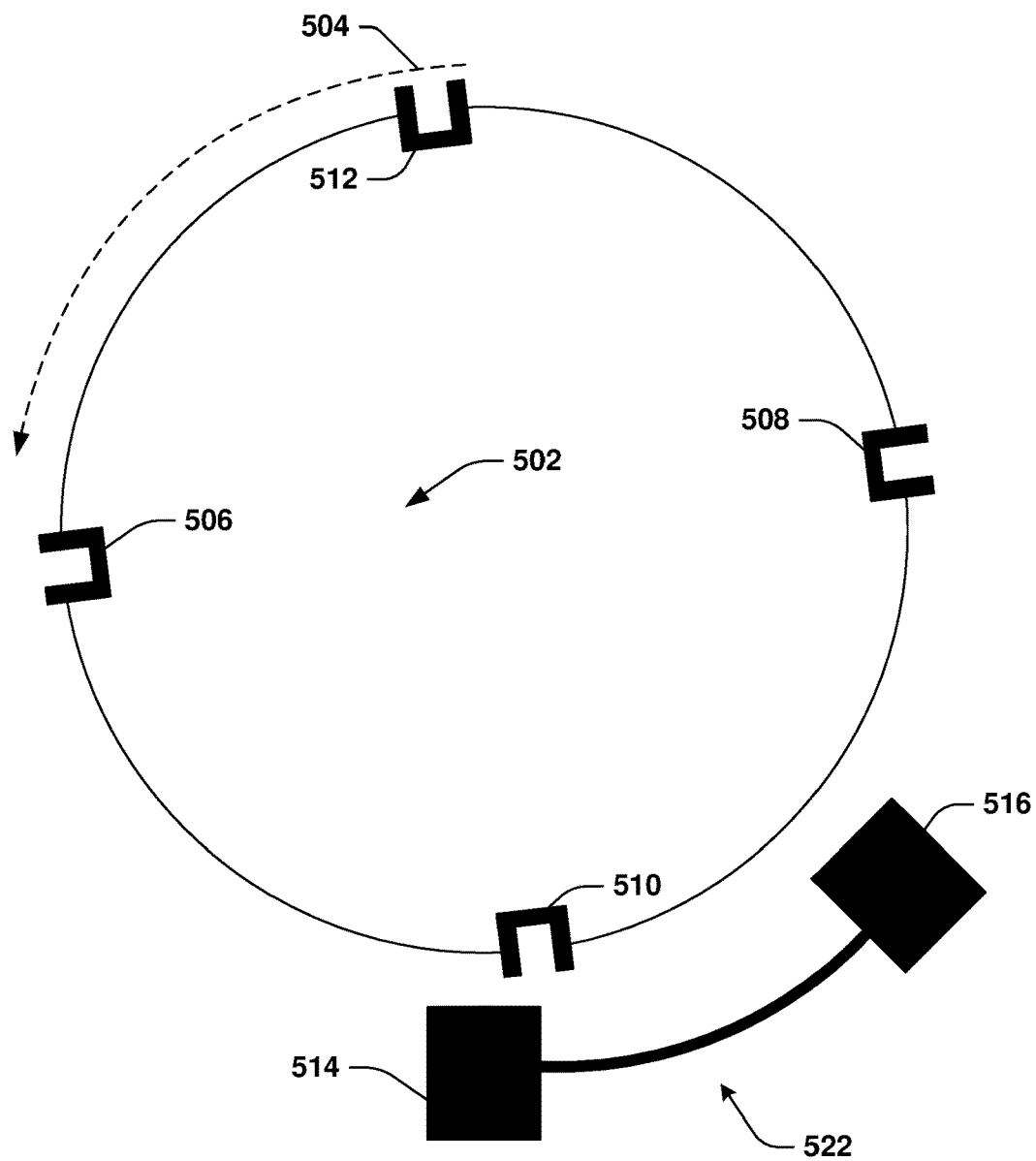
FIG. 5G illustrates example technique for setting a sampling frequency for a radiation imaging system, where a clock frequency is set.
Figure 5G:
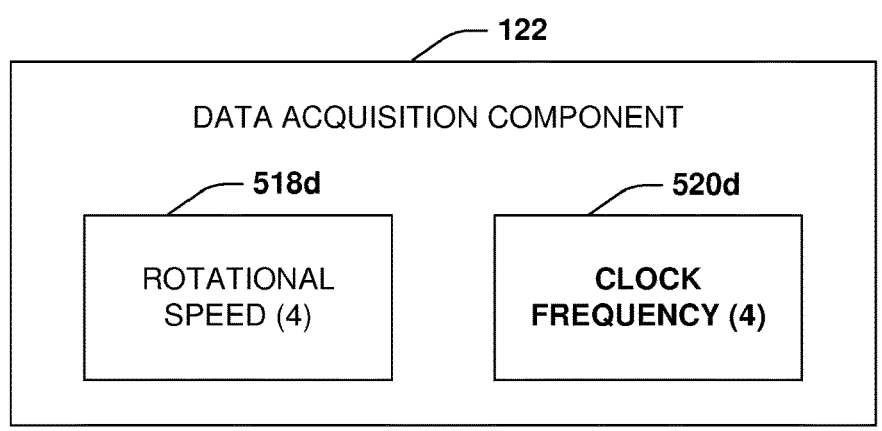

FIG. 5G illustrates the rotating gantry 502 at a seventh position after a certain amount of rotation 504. The third sensor 510 finishes encountering the first flag structure 514 (e.g., an instance at which the optical beam from the third sensor 510 is no longer interrupted/broken by the first flag structure 514), which is detected as a falling edge of the third pulse. Accordingly, a fourth clock frequency 520d is set for the clock based upon the fourth current rotational speed 518d and/or other data such as a desired number of views remaining to capture. The fourth clock frequency 520d establishes a fourth sampling frequency used to sample detector cells (e.g., capture samples/views) until a next encounter of a flag structure by a sensor (e.g., the third sensor 510 encountering the second flag structure 516). In some embodiments, if the fourth current rotational speed 518d indicates an increase in rotational speed, then the fourth clock frequency 520d may be set as an increased frequency value so that a desired number of views can still be captured. If the fourth current rotational speed 518d indicates a decrease in rotational speed, then the fourth clock frequency 520d may be set as a decreased frequency value so that unnecessary views beyond the desired number of views are not captured.

Because there are 4 sensors and 2 flag structures, there will be 8 encounters of a sensor encountering a flag structure during a revolution of the rotating gantry 502. Thus, there will be 8 pulses that can be used as opportunities to determine current rotational speed and to adjust the sampling frequency based upon such. It may be appreciated that any number of sensors at any locations and/or any number of flag structures at any locations may be used.

It may be appreciated that by using a plurality of sensors and a plurality of flag structures, a system can be devised that effective provides one logically continuous pulse stream that can be used to adjust the sampling timing. The length of the partial arc segment (e.g., between the first flag structure 514 and the second flag structure 516 or between a beginning of a flag structure and an end of the same flag structure) and the number of sensors (and their relative positions along the rotating gantry 502) can be selected such that there is always one sensor 506, 508, 510, 512 that is within the partial arc segment (e.g., between the first flag structure 514 and the second flag structure 516) that can be used to measure the current rotational speed.

Figure 6:
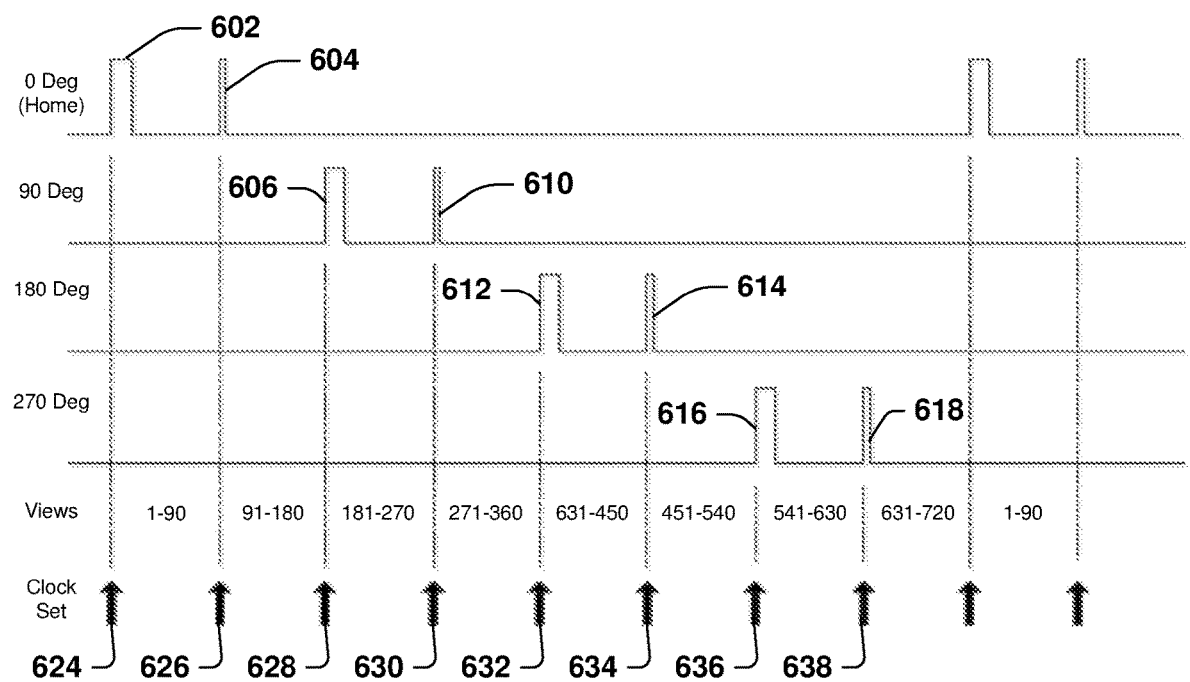
FIG. 6 is an illustration of a set of pulses corresponding sensors encountering flag structures.

FIG. 6 illustrates a set of pulses corresponding sensors encountering flag structures. In some embodiments, 720 views are to be captured during a revolution of a rotating gantry. A first sensor may be positioned at a 0 degree home position, a second sensor may be positioned at a 90 degree position, a third sensor may be positioned at a 180 degree position, and a fourth sensor may be positioned at a 270 degree position relative a stationary support. A first flag structure and a second flag structure may be positioned relative to the rotating gantry along a partial arc segment (e.g., an arc shaped structure that is less than a full 360 degree structure). The first flag structure may have a width that is wider than the second flag structure, and thus an encounter of a sensor with the first flag structure is longer and results in a longer pulse width than an encounter with the second flag structure.

During a revolution of the rotating gantry, the first sensor may encounter the first flag structure. The encounter results in a first pulse 602 having a first pulse width indicative of a width/size of the first flag structure. Accordingly, a first current rotational speed is determined. The first current rotational speed is used to set a first clock frequency 624 of a clock to establish a first sampling frequency for sampling detector cells (e.g., for obtaining views 1-90).

Next, during the revolution of the rotating gantry, the first sensor may encounter the second flag structure. The encounter results in a second pulse 604 having a second pulse width indicative of a width/size of the second flag structure. Accordingly, a second current rotational speed is determined. The second current rotational speed is used to set a second clock frequency 626 of the clock to establish a second sampling frequency for sampling detector cells (e.g., for obtaining views 91-180).

Next, during the revolution of the rotating gantry, the second sensor may encounter the first flag structure. The encounter results in a third pulse 606 having the first pulse width indicative of the width/size of the first flag structure. Accordingly, a third current rotational speed is determined. The third current rotational speed is used to set a third clock frequency 628 of the clock to establish a third sampling frequency for sampling detector cells (e.g., for obtaining views 181-270).

Next, during the revolution of the rotating gantry, the second sensor may encounter the second flag structure. The encounter results in a fourth pulse 610 having the second pulse width indicative of the width/size of the second flag structure. Accordingly, a fourth current rotational speed is determined. The fourth current rotational speed is used to set a fourth clock frequency 630 of the clock to establish a fourth sampling frequency for sampling detector cells (e.g., for obtaining views 271-360).

Next, during the revolution of the rotating gantry, the third sensor may encounter the first flag structure. The encounter results in a fifth pulse 612 having the first pulse width indicative of the width/size of the first flag structure. Accordingly, a fifth current rotational speed is determined. The fifth current rotational speed is used to set a fifth clock frequency 632 of the clock to establish a fifth sampling frequency for sampling detector cells (e.g., for obtaining views 361-450).

Next, during the revolution of the rotating gantry, the third sensor may encounter the second flag structure. The encounter results in a sixth pulse 614 having the second pulse width indicative of the width/size of the second flag structure. Accordingly, a sixth current rotational speed is determined. The sixth current rotational speed is used to set a sixth clock frequency 634 of the clock to establish a sixth sampling frequency for sampling detector cells (e.g., for obtaining view 451-540).

Next, during the revolution of the rotating gantry, the fourth sensor may encounter the first flag structure. The encounter results in a seventh pulse 616 having the first pulse width indicative of the width/size of the first flag structure. Accordingly, a seventh current rotational speed is determined. The seventh current rotational speed is used to set a seventh clock frequency 636 of the clock to establish a seventh sampling frequency for sampling detector cells (e.g., for obtaining views 541-630).

Next, during the revolution of the rotating gantry, the fourth sensor may encounter the second flag structure. The encounter results in an eighth pulse 618 having the second pulse width indicative of the width/size of the second flag structure. Accordingly, an eighth current rotational speed is determined. The eighth current rotational speed is used to set an eighth clock frequency 638 of the clock to establish an eighth sampling frequency for sampling detector cells (e.g., for obtaining view 631-720).

In this way, the revolution of the rotating gantry is complete. During the revolution, 8 encounters between sensors and flag structures occurred. The 8 encounters result in 8 pulses, and thus 8 opportunities to adjust the sampling frequency for obtaining views of the 720 views. The sampling frequency is adjusted dynamically to compensate for rotational speed changes of the rotating gantry so that the 720 views are still obtained by the end of the revolution.

As described with respect to FIG. 2, one or more flag structures and one or more sensors are used to generate pulses when sensors encounter flag structures, and the example method 700 may use these pulses as opportunities to set/adjust a clock frequency that establishes a sampling frequency used by a data acquisition system to sample detector cells of a detector array.

At 702 in the example method 700, a first pulse, detected by a first sensor disposed on a rotating gantry of a radiation imaging system, is identified. In some embodiments, a first width of the first pulse is identified as corresponding to a first size of a first flag structure. In this way, a determination can be made as to a current position of the rotating gantry as having an orientation where the first sensor is facing the first flag structure.

At 704 in the example method 700, a first current rotational speed of the rotating gantry is determined. The first current rotational speed may be determined using various techniques, such as an analysis of an amount of time elapsed since a last flag structure was encountered by a sensor and/or distances between flag structures and/or sensors. In some embodiments, the first current rotational speed is determined upon detecting a rising edge of the first pulse or at any other time.

At 706 in the example method 700, a clock frequency of a clock is set based upon the first current rotational speed. The clock frequency establishes a first sampling frequency for the data acquisition system of the radiation imaging system for samples taken between an identification of the first pulse and an identification of a next pulse (e.g., a next encounter of a sensor with a flag structure). The clock frequency may be set based upon the first rotational speed and a desired number of samples (e.g., views) to obtain during a next sampling segment between the first pulse and the next pulse. For example, if rotation of the rotating gantry has increased from an expected value, then the clock frequency is increased so that the desired number of samples can still be obtained. Otherwise, the rotating gantry will travel quicker through the next sampling segment and less than the desired number of samples may be obtained. In some embodiments, the clock frequency is set upon detecting a falling edge of the first pulse or at any other time.

At 708 in the example method 700, a second pulse, detected by a second sensor disposed on the rotating gantry of the radiation imaging system, is identified. It may be appreciated that in one example, the second pulse may be detected by the first sensor depending on the number of sensors and flag structures and/or the positioning of such. In some embodiments, a second width of the second pulse is identified as corresponding to the first size of the first flag structure. In other embodiments, the second width of the second pulse is identified as corresponding to a second size of a second flag structure. In this way, a determination can be made as to a current position of the rotating gantry as having an orientation where the second sensor is facing a particular flag structure.

At 710 in the example method 700, a second current rotational speed of the rotating gantry is determined. The second current rotational speed may be determined using various techniques, such as an analysis of an amount of time elapsed since a last flag structure was encountered by a sensor (e.g., the first sensor encountering a flag structure to generating the first pulse) and/or distances between flag structures and/or sensors. In some embodiments, the second current rotational speed is determined upon detecting a rising edge of the second pulse or at any other time.

At 712 in the example method 700, the clock frequency of the clock is set based upon the second current rotational speed. The clock frequency establishes a second sampling frequency for the data acquisition system of the radiation imaging system for samples taken between an identification of the second pulse and an identification of a second next pulse (e.g., a next encounter of a sensor with a flag structure). The clock frequency may be set based upon the second rotational speed and a desired number of samples (e.g., views) to obtain during the next sampling segment between the second pulse and the second next pulse. For example, if rotation of the rotating gantry has decreased from an expected value, then the clock frequency is decreased so that the desired number of samples can be obtained. Otherwise, the rotating gantry will travel slower through the next sampling segment and more than the desired number of samples may be obtained. In some embodiments, the clock frequency is set upon detecting a falling edge of the second pulse or at any other time.

It may be appreciated that in one example, the example method 700 may be performed as a continuous loop of identifying pulses, determining current rotational speed, and setting clock frequencies. The continuous loop is performed as the rotating gantry rotating any number of times around an object under examination. Moreover, the example method 700 can be performed using any number of flag structures and/or any number of sensors.

Figure 7:
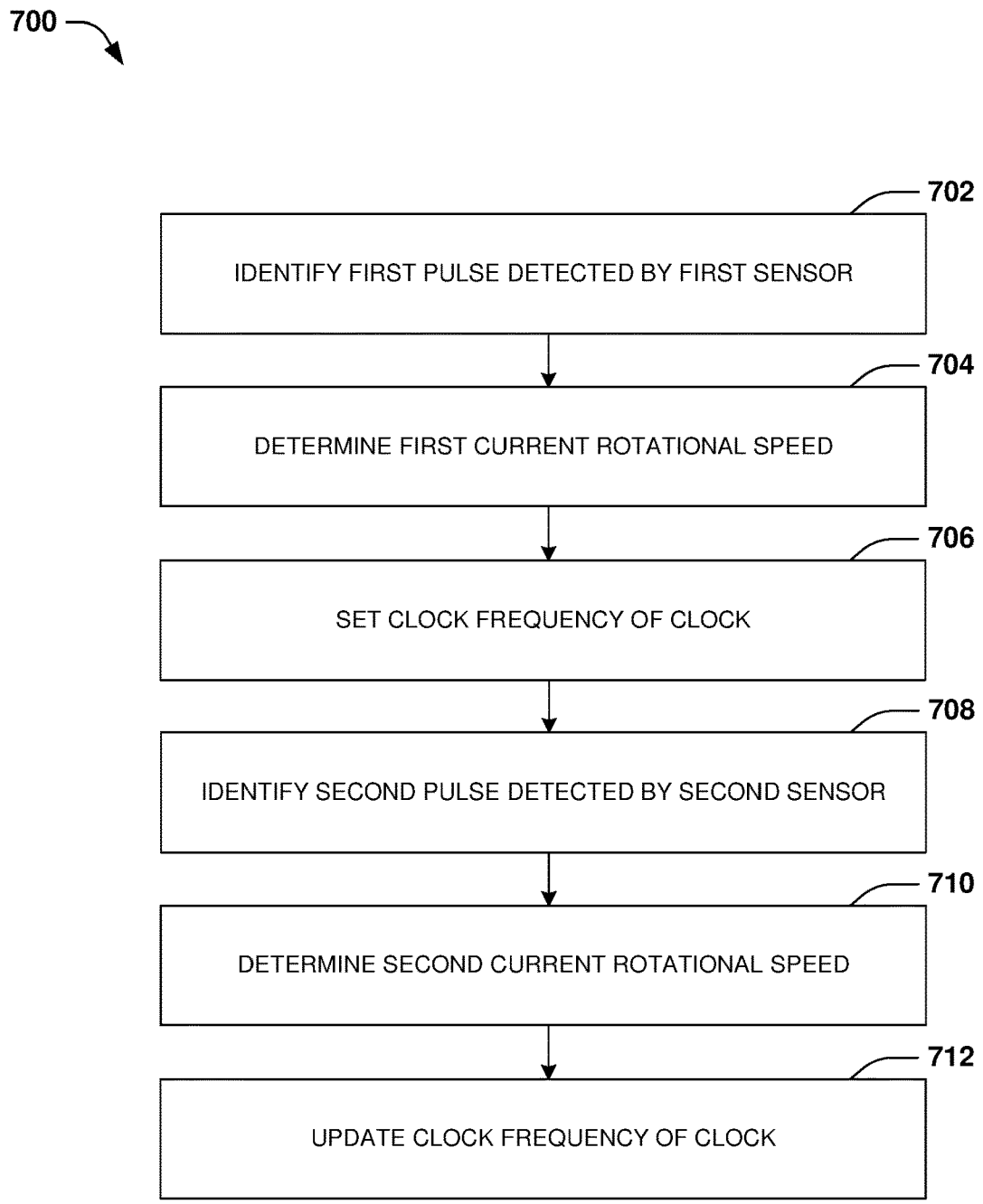
FIG. 7 illustrates example method for setting a sampling frequency for a radiation imaging system.
Figure 8:
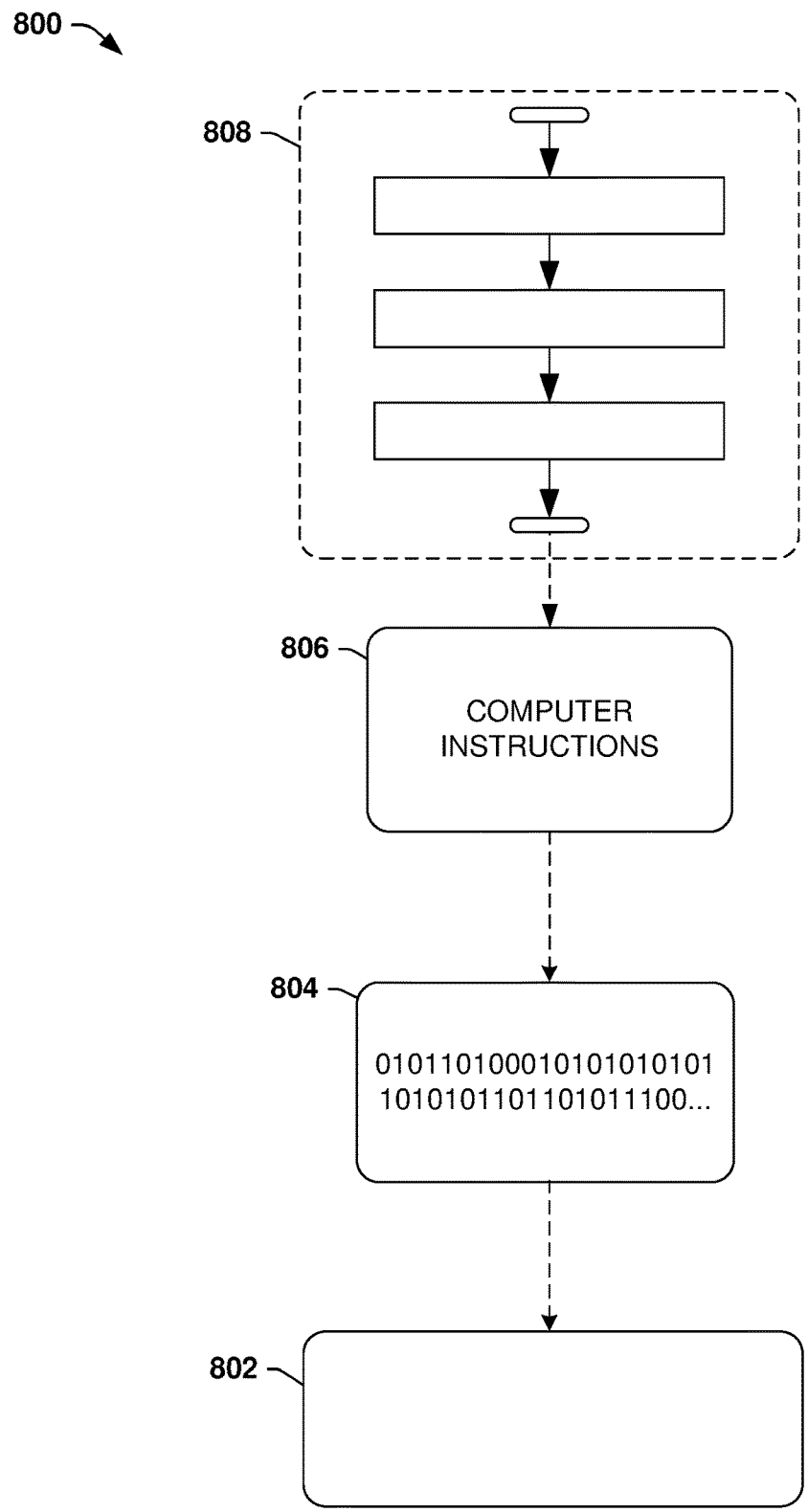
FIG. 8 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 8, wherein the implementation 800 comprises a computer-readable medium 802 (e.g., a flash drive, CD-R, DVD-R, application-specific integrated circuit (ASIC), field-programmable gate array (FPGA), a platter of a hard disk drive, etc.), on which is encoded computer-readable data 804. This computer-readable data 804 in turn comprises a set of processor-executable instructions 806 configured to operate according to one or more of the principles set forth herein. In one such embodiment 800, the processor-executable instructions 806 may be configured to perform a method 808 when executed via a processing unit, such as at least some of the example method 700 of FIG. 7. In another such embodiment, the processor-executable instructions 806 may be configured to implement a system, such as at least some of the example system 100 of FIG. 1. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or. " In addition, "a" and "an" as used in this disclosure are generally to be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

As used in this disclosure, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A radiation imaging system comprising:
    a set of sensors disposed on one of a rotating gantry or a stationary support about which the rotating gantry rotates;
    a first flag structure disposed relative to the other of the rotating gantry or the stationary support of the radiation imaging system; and
    a data acquisition system configured to:
        upon a sensor of the set of sensors encountering the first flag structure:
            determine a current rotational speed of the rotating gantry; and
            set a clock frequency of a clock based upon the current rotational speed, wherein the clock frequency establishes a sampling frequency for the data acquisition system of the radiation imaging system for samples taken between an encounter with the first flag structure and an encounter with a next flag structure.

2. The radiation imaging system of claim 1, comprising a second flag structure, and the data acquisition system configured to:
    upon the sensor encountering the second flag structure:
        determine a new current rotational speed of the rotating gantry; and
        update the clock frequency based upon the new current rotational speed.

3. The radiation imaging system of claim 1, the data acquisition system configured to:
    upon a second sensor of the set of sensors encountering the first flag structure:
        determine a new current rotational speed of the rotating gantry; and
        update the clock frequency based upon the new current rotational speed.

4. The radiation imaging system of claim 1, comprising a second flag structure, wherein the first flag structure and the second flag structure have a same size.

5. The radiation imaging system of claim 1, comprising a second flag structure, wherein the first flag structure has a first size and the second flag structure has a second size different than the first size.

6. The radiation imaging system of claim 5, wherein the data acquisition system is configured to:
determine a current position of the rotating gantry based upon determining that a flag structure traversed by the sensor has the first size and not the second size.

7. The radiation imaging system of claim 1, wherein the data acquisition system is configured to:
determine a size of a flag structure based upon a width of a pulse detected by the sensor.

8. The radiation imaging system of claim 1, wherein a plurality of flag structures are positioned according to a partial arc segment.

9. The radiation imaging system of claim 8, wherein a flag structure of the plurality of flag structures is designated as a home position.

10. A radiation imaging system comprising:
an ionizing radiation source;
a detector array comprising a plurality of detector cells configured to detect radiation emitted by the ionizing radiation source;
a data acquisition system electrically coupled to the detector array and configured to sample the plurality of detector cells according to a sampling frequency;
a rotating gantry upon which the ionizing radiation source and the detector array are mounted;
a stationary support;
a set of sensors disposed on one of the rotating gantry or the stationary support; and
a set of flag structures disposed relative to the other of the rotating gantry or the stationary support and spaced apart to define a partial arc segment, wherein the data acquisition system is configured to:
upon a sensor of the set of sensors encountering a flag structure of the set of flag structures that begins a first partial arc segment portion of the partial arc segment:
determine a current rotational speed of the rotating gantry; and
set a clock frequency of a clock based upon the current rotational speed.

11. The radiation imaging system of claim 10, wherein a first flag structure of the set of flag structures has a first size and a second flag structure of the set of flag structures has a second size different than the first size.

12. The radiation imaging system of claim 11, the data acquisition system configured to:
detect traversal of the first flag structure based upon a width, of a pulse detected by the sensor, indicative of the first size; and
determine a current location of the rotating gantry based upon detecting traversal of the first flag structure.

13. The radiation imaging system of claim 10, the data acquisition system configured to:
upon identifying a rising edge of a pulse detected by the sensor, determine the current rotational speed; and
upon identifying a falling edge of the pulse detected by the sensor, set the clock frequency.

14. The radiation imaging system of claim 10, wherein the sensor is an optical sensor.

15. The radiation imaging system of claim 10, wherein the set of flag structures comprise a first flag structure and a second flag structure, the first flag structure positioned 45 degrees from the second flag structure.

16. The radiation imaging system of claim 10, wherein the set of flag structures comprise a first flag structure, a second flag structure, and a third flag structure, the first flag structure positioned 30 degrees from the second flag structure and the second flag structure positioned 30 degrees from the third flag structure.

17. A method for setting a sampling frequency for a radiation imaging system, the method comprising:
upon identifying a first pulse detected by a first sensor disposed on one of a rotating gantry or a stationary support about which the rotating gantry rotates:
determining a first current rotational speed of the rotating gantry;
setting a clock frequency of a clock based upon the first current rotational speed, wherein the clock frequency establishes a first sampling frequency for a data acquisition system of the radiation imaging system for samples taken between an identification of the first pulse and an identification of a next pulse; and
upon identifying a second pulse detected by a second sensor:
determining a second current rotational speed of the rotating gantry; and
updating the clock frequency of the clock to an updated clock frequency based upon the second current rotational speed, wherein the updated clock frequency establishes a second sampling frequency for the data acquisition system of the radiation imaging system for samples taken between identification of the second pulse and an identification of a second next pulse.

18. The method of claim 17, comprising:
determining the first current rotational speed upon detecting a rising edge of the first pulse.

19. The method of claim 17, comprising:
setting the clock frequency upon detecting a falling edge of the first pulse.

20. The method of claim 17, comprising:
identifying a first width of the first pulse as corresponding to a first size of a first flag structure; and
identifying a second width of the second pulse as corresponding to a second size, different than the first size, of a second flag structure.

* * * * *